(12) United States Patent
Swager et al.

(10) Patent No.: US 10,160,715 B2
(45) Date of Patent: Dec. 25, 2018

(54) MECHANOCHEMICAL SYNTHESIS OF IPTYCENES

(71) Applicant: Massachusetts Institute of Technology, Cambridge, MA (US)

(72) Inventors: Timothy M. Swager, Newton, MA (US); Yanchuan Zhao, Cambridge, MA (US); Silvia Veleirinho de Oliveira Rocha, Zurich (CH)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 15/249,061

(22) Filed: Aug. 26, 2016

(65) Prior Publication Data

US 2018/0057443 A1 Mar. 1, 2018
US 2018/0244602 A9 Aug. 30, 2018

(51) Int. Cl.
| | | |
|---|---|---|
| C07C 67/293 | (2006.01) | |
| C07C 69/604 | (2006.01) | |
| B01D 53/02 | (2006.01) | |
| B01J 20/26 | (2006.01) | |

(52) U.S. Cl.
CPC .......... *C07C 69/604* (2013.01); *B01D 53/02* (2013.01); *B01J 20/261* (2013.01); *C07C 67/293* (2013.01); *B01D 2253/20* (2013.01)

(58) Field of Classification Search
CPC ................................ C08G 61/02; C08G 61/21
See application file for complete search history.

(56) References Cited

U.S. PATENT DOCUMENTS

| | | | |
|---|---|---|---|
| 7,494,698 B2 | 2/2009 | Swager et al. | |
| 2002/0150697 A1* | 10/2002 | Swager ................. | C08G 61/02 428/1.1 |

OTHER PUBLICATIONS

Zaragoza Dorwald, Side Reactions in Organic Synthesis, 2005, WILEY-VCH Verlag GmbH & Co. KGaA, Weinheim, Preface. p. IX.*
Baláž et al, Chemical Society Reviews, Hallmarks of Mechanochemistry: from Nanoparticles to Technology, 2013, 42, pp. 7571-7637.*
Shalai et al, Journal of Organic Chemistry, Synthesis of Supertriptycene and Two Related Iptycenes, 1991, 56, pp. 6905-6912.*
Invitation to Pay Additional Fees dated May 24, 2017 for Application No. PCT/US2016/049043.
International Search Report and Written Opinion dated Jul. 18, 2017 for Application No. PCT/US2016/049043.
Bartlett et al., Triptycene[1] (9,10-o-Benzenoanthracene). J Am Chem Soc. Nov. 1942;64(11):2649-53. doi: 10.1021/ja01263a035.
Chen et al., Rapid mechanochemical preparation of a sandwich-like charge transfer complex. Cryst Eng Comm. 2013;15(22):4413-6.
Chen et al., Highly emissive iptycene—fluorene conjugated copolymers: synthesis and photophysical properties. Macromolecules. Aug. 2008;41(13):6672-6. doi: 10.1021/ma800486a.
Chong et al.,. Iptycenes in supramolecular and materials chemistry. Chem Soc Rev. Dec. 2009;38(12):3301-15. doi: 10.1039/b900754g. Epub Jul. 20, 2009.
Ghanem et al., A triptycene-based polymer of intrinsic microposity that displays enhanced surface area and hydrogen adsorption. Chem Commun (Camb). Jan. 7, 2007;1:67-9. Epub Nov. 15, 2006.
Ghanem et al., Triptycene-based polymers of intrinsic microporosity: organic materials that can be tailored for gas adsorption. Macromolecules. May 2010;43(12):5287-94. doi: 10/1021/ma100640m.
Gould et al., Combined Lewis acid and Brønsted acid-mediated reactivity of glycosyl trichloroacetimidate donors. Carbohydr Res. Dec. 15, 2013;382:36-42. doi: 10.1016/j.carres.2013.09.011. Epub Oct. 10, 2013.
Hart et al., Generalization of the triptycene concept. Use of diaryne equivalents in the synthesis of iptycenes. J Org Chem. Oct. 1981;46(22):4427-32. doi: 10.1021/jo00335a021.
Hart, Iptycenes, cuppendophanes and cappedophanes. Pure and Applied Chemistry. 1993; 65(1):27-34.
Hua et al., Syntheses and bioactivities of substituted 9,10-dihydro-9,10-[1,2]benzenoanthracene-1,4,5,8-tetrones. Unusual reactivities with amines. J Org Chem. May 3, 2002;67(9):2907-12.
Kelly, Progress toward a rationally designed molecular motor. Acc Chem Res. Jun. 2001;34(6):514-22.
McKissic et al., Comparison of shaking versus baking: further understanding the energetics of a mechanochemical reaction. Green Chem. 2014;16(3):1628-32.
Patney, A general and simple route to the synthesis of triptycenes. Synthesis. Sep. 1991;1991(9):694-6.
Pradipta et al., Semiempirical computation of the solid phase Diels-Alder reaction between anthracene derivatives and p-benzoquinone via molecular distortion. Solid State Ionics. 2004;172(1-4):169-72.
Reinhard et al., Synthesis of triphenylene-based triptycenes via suzuki-miyaura cross-coupling and subsequent scholl reaction. J Org Chem. Sep. 18, 2015;80(18):9342-8. doi: 10.1021/acs.joc. 5b01520. Epub Aug. 28, 2015.
Senna, Ecological mechanochemistry-rational utilization of cross-boundary charge transfer. J Soc Powder Technol. 2008;45(8)556-63.
Sereda et al., Synthesis of bicyclic quinones via 1,4-diacetoxyanthracene. Tetrahedron Lett. Dec. 11, 2006;47(50):8901-3.
Shahlai et al., Synthesis of supertriptycene and two related iptycenes. Journal of Organic Chemistry. 1991;56:6905-12.

(Continued)

*Primary Examiner* — Paul A Zucker
(74) *Attorney, Agent, or Firm* — Wolf, Greenfield & Sacks, P.C.

(57) ABSTRACT

Methods for mechanochemically synthesizing compositions comprising bridged bicyclic-based compounds such as iptycene-based compounds are generally provided. In some cases, two or more polycyclic aromatic hydrocarbons may be mechanochemically reacted such that the product comprises the bridged bicyclic-based compound. In some embodiments, the product (e.g., the bridged bicyclic compound) may comprise two or more [2.2.2] bicyclic cores. In certain embodiments, the mechanochemical reactions described herein may produce higher order bridged bicyclic-based compounds such as oligoiptcyenes or poly-iptycenes. In certain embodiments, the bridged bicyclic based compound comprises a molecular cage.

13 Claims, 16 Drawing Sheets

(56) References Cited

OTHER PUBLICATIONS

Strukil et al., Trapping reactive intermediates by mechanochemistry: elusive aryl n-thiocarbamoylbenzotriazoles as bench-stable reagents. Angew Chem Int Ed Engl. Jul. 13, 2015;54(29):8440-3. doi: 10.1002/anie.201502026. Epub Jun. 9, 2015.

Swager, Iptycenes in the design of high performance polymers. Acc Chem Res. Sep. 2008;41(9):1181-9. doi: 10.1021/ar800107v. Epub Aug. 30, 2008.

Tao et al., Tailoring the synergistic bronsted-lewis acidic effects in heteropolyacid catalysts: applied in esterification and transesterification reactions. Sci Rep. Sep. 16, 2015;5:13764(1-10). doi: 10.1038/srep13764.

Wang, Mechanochemical organic synthesis. Chem Soc Rev. Sep. 21, 2013;42(18):7668-700. doi: 10.1039/c3cs35526h. Epub May 9, 2013.

Wang et al., [60]Fullerene adducts with 9-substituted anthracenes: mechanochemical preparation and retro Diels-Alder reaction. Tetrahedron. May 16, 2005;61(20):4851-6.

Watanabe et al., Acceleration of solid state Diels—Alder reactions by incorporating the reactants into crystalline charge transfer complexes. Tetrahedron Lett. Oct. 3, 2005;46(40):6815-18.

Yang et al., Porous shape persistent fluorescent polymer films: an approach to TNT sensory materials. J Am Chem Soc. May 1998;120(21):5321-2. doi: 10.1021/ja9742996.

Yang et al., Solid-state molecular folding and supramolecular structures of triptycene-derived secondary dicarboxamides. J Org Chem. Oct. 18, 2002;67(21):7343-54.

Zhang et al., Mechanochemical Diels-Alder cycloaddition reactions for straightforward synthesis of endo-Norbornene derivatives. Syn Lett. 2010;2010(19):2895-8. doi: 10/1055/s-0030-1259030.

Zhao et al., Mechanochemical synthesis of extended iptycenes. J Am Chem Soc. Oct. 14, 2016;138(42):13834-7.

Zhao et al., Conjugated polymers containing large soluble diethynyl iptycenes. Org Lett. Sep. 29, 2005;7(20):4357-60.

Zhu et al., Iptycene quinones: synthesis and structure. J Org Chem. Feb. 4, 2005;70(3):917-24. Epub Dec. 24, 2004.

* cited by examiner 4d, 60 % yield 4c, 75 % yield 4b, 85 % yield

MECHANOCHEMICAL SYNTHESIS OF IPTYCENES

FIELD OF THE INVENTION

This invention generally relates to mechanochemical synthesis of compositions and articles comprising bridged bicyclic compounds such as iptycene-based compounds.

BACKGROUND OF THE INVENTION

Iptycenes are structural motifs of great interest as a result of their rigid noncompliant three-dimensional architecture. The preparation of larger iptycenes is often problematic as a result of their limited solubility and synthetic procedures involving multiple Diels-Alder reactions under harsh extended reaction conditions. Accordingly, improved methods and compositions are needed.

SUMMARY OF THE INVENTION

The present invention generally relates to mechanochemical synthesis of compositions and articles comprising bridged bicyclic compounds such as iptycene-based compounds. Certain of the compositions described herein include a polyiptycenes.

In one aspect, methods for forming a composition are provided. In some embodiments, the method comprises mechanochemically reacting a first polycyclic aromatic hydrocarbon composition with a second polycyclic aromatic hydrocarbon composition different than the first polycyclic aromatic hydrocarbon composition to form a product, wherein the product comprises a bridged bicyclic-based compound comprising two or more [2.2.2] bicyclic cores.

In another aspect, compositions are provided. In some embodiments, the composition comprises a bridged bicyclic-based compound wherein at least a portion comprises a molecular cage having a first group attached to a first [2.2.2] bicyclic core and a second group attached to a second [2.2.2] bicyclic core, further comprising a fixed distance between the first group and the second group of less than or equal to 9.5 Å.

Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention. In the figures.

DETAILED DESCRIPTION OF THE INVENTION

Figure 1A:
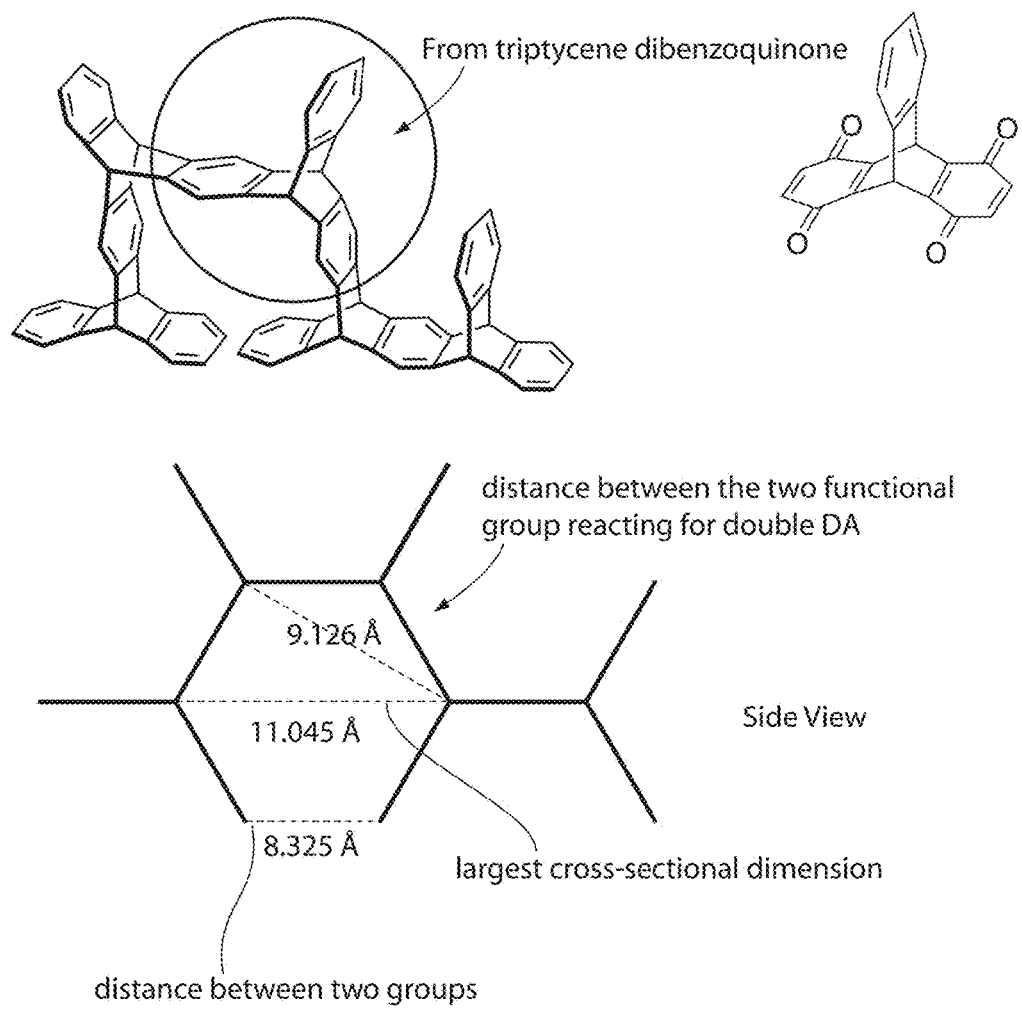
FIG. 1A shows an illustrative embodiment of determining a fixed distance in a bridged bicyclic compound, according to one set of embodiments.

Methods for mechanochemically synthesizing compositions comprising bridged bicyclic-based compounds such as iptycene-based compounds are generally provided. In some cases, two or more polycyclic aromatic hydrocarbons may be mechanochemically reacted such that the product comprises the bridged bicyclic-based compound. In some embodiments, the product (e.g., the bridged bicyclic compound) may comprise two or more [2.2.2] bicyclic cores. In certain embodiments, the mechanochemical reactions described herein may produce higher order bridged bicyclic-based compounds such as poly-iptycenes (e.g., an extended iptycene). In certain embodiments, the bridged bicyclic based compound comprises a molecular cage. The compounds and methods described herein may be useful in various applications including, for example, chemical sensing, absorption of toxic compounds (e.g., toluene, benzene), and/or filtration.

Advantageously, the methods described herein may be iterative such that compositions may be grown in sequence. In some embodiments, the product of the mechanochemical reactions described herein may be isolated and/or purified with a simple washing and/or precipitation step (e.g., without the need for a separate chromatographic separation step).

In some embodiments, the method comprises mechanochemically reacting two or more polycyclic aromatic hydrocarbon compositions to form a product. In certain embodiments, the mechanochemical reaction comprises a bridged bicyclic-based compound (e.g., a bridged bicyclic-based compound comprising two or more [2.2.2] bicyclic cores). Mechanochemically reacting two or more polycyclic aromatic hydrocarbon compositions comprises, in some embodiments, chemically reacting (e.g., via Diels-Alder reaction) a first polycyclic aromatic hydrocarbon composition and a second polycyclic aromatic hydrocarbon composition in the presence of a mechanical force. In some embodiments, the mechanical force may be generated by, for example, mechanical milling (e.g., ball milling).

Advantageously, the use of mechanical milling in combination with the chemical reaction may reduce the reaction time, lower the reaction temperature, increase product yield, and/or reduce and/or eliminate the need for reactive catalysts as compared to the use of chemical reactions alone. In some embodiments, the methods described herein form relatively high number average molecular weight (e.g., greater than 1000 Da) compounds such as high order polyiptycenes (i.e. extended iptycenes).

In some embodiments, the method comprises mechanochemically reacting two or more polycyclic aromatic hydrocarbon compositions in the presence of an additive to form the bridged bicyclic-based compound. Non-limiting examples of suitable additives include Lewis acids, Brønsted acids, transition metals (e.g., Zn) and halides thereof, acid anhydrides, and acid chlorides. Non limiting examples of suitable Lewis acids include $Li^+$, $Na^+$, $K^+$, $Al^{3+}$, $Mg^{2+}$, $Ca^{2+}$, $BF_3$, $SnCl_4$, $Ti(OiPr)_4$, $Al(CH_3)_3$, and $AlCl_3$. Those skilled in the art would be capable of selecting suitable additional Lewis acids based upon the teachings of this specification. Advantageously, the mechanochemical reaction of two or more polycyclic aromatic hydrocarbon compositions described herein in the presence of an additive such as a Lewis acid include, for example, increased yield and/or increased reaction time as compared to the reaction in the absence of such additives.

In some embodiments, the first polycyclic aromatic hydrocarbon composition comprises anthracene, optionally substituted. In certain embodiments, the second polycyclic aromatic hydrocarbon composition comprises an anthraquinone, optionally substituted or a benzoquinone, optionally substituted. Non-limiting examples of suitable polycyclic aromatic hydrocarbons include 1,4-anthraquinone, 1,4-benzoquinone, 9,10-dihydro-9,10-(o-benzeno)anthracene-1,4,5,8-tetraone, or 9,10-dihydro-9,10-[1,2]benzenoanthracene-13,16-dione.

The bridged bicyclic compounds described herein generally comprise the structure as in Formula (I):

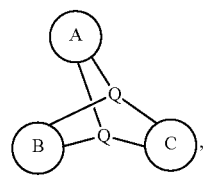

(I)

wherein A, B, and C are the same or different and at least two of A, B, and C include an aromatic hydrocarbon and Q is a tetrahedral bridgehead group. For example, in some embodiments, the bridged bicyclic compound is a [2.2.1] bridged bicyclic compound having a structure as in Formula (I) wherein A and B are the same or different and comprise an aromatic group, and C is oxygen, NR, or $CR_2$, where R is H or phenyl. In certain embodiments, the bridged bicyclic compound is a [2.2.2] bridged bicyclic compound having a structure as in Formula (I) wherein A, B, and C are the same or different and include aromatic groups. In some embodiments, Q is CH.

In some embodiment, the compositions described herein comprise a bridged bicyclic-based compound comprising two or more [2.2.2] bicyclic cores. For example, in some embodiments, at least one of A, B, and C are attached to a second bridged bicyclic compound. In certain embodiments, the bridged bicyclic-based compounds described herein may comprise a first bridged bicyclic compound bound to a second bridged bicyclic compounds, each bridged bicyclic compound comprising a structure as in Formula (I).

In some embodiments, at least one of the two or more [2.2.2] bicyclic cores has the following structure:

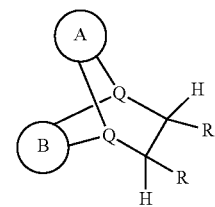

wherein each R can be the same or different and are hydrogen, halo, hydroxyl, amino, alkyl, heteroalkyl, alkenyl, alkynyl, aryl, heteroaryl, heterocyclyl, or a carbonyl group, any of which is optionally substituted, or can be joined together to form an optionally substituted ring. Non-limiting examples of suitable [2.2.2] bicyclic cores include:

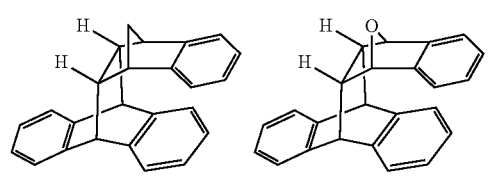

Non-limiting examples of suitable bridged bicyclic-based compounds are shown in FIGs. 3-7.

In some embodiments, at least one of the two or more [2.2.2] bicyclic cores has the following structure:

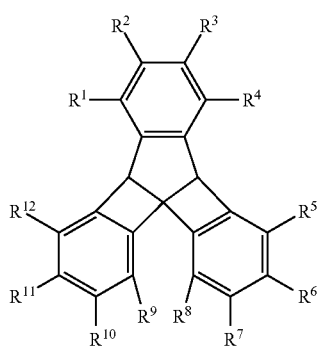

wherein:

R$^1$-R$^{12}$ can be the same or different and are hydrogen, halo, hydroxyl, amino, alkyl, heteroalkyl, alkenyl, alkynyl, aryl, heteroaryl, heterocyclyl, or a carbonyl group, any of which is optionally substituted, or, any two adjacent groups of R$^1$-R$^{12}$ can be joined together to form an optionally substituted ring.

In some embodiments, at least one of the two or more [2.2.2] bicyclic cores is an iptycene core. For example, some embodiments provide compositions including an iptycene-based compound comprising two or more iptycene cores. In certain embodiments, the composition comprises and one or more optionally substituted heterocyclyl or optionally substituted heteroaryl moieties rigidly bonded to at least one iptycene-based core. In some cases, a group may be rigidly bonded to a core such that the group does not easily rotate about a bond axis, e.g., a bond that binds the group to the core. In one embodiment, the group rotates no more than about 180°, no more than about 120°, no more than about 60°, no more than about 30°, or less, about a bond that binds the group to the core. In some cases, a group may be rigidly bound to the core via two covalent bonds. For example, a group may be fused to the core via covalent bonds to two adjacent atoms of the core.

In some cases, the heterocyclyl or heteroaryl moiety may be rigidly bonded to at least one iptycene core and/or may define at least a portion of at least one iptycene core. For example, one or more iptycene cores may include one or more phenyl rings that may be extended or functionalized so as to form a heterocyclyl or heteroaryl moiety (e.g., a carbazole group) which includes one or more phenyl rings of each iptycene core.

In some embodiments, the iptycene-based compound includes a triptycene core. In some embodiments, the iptycene-based compound includes a pentiptycene core. It should be understood that the compound may include other, extended iptycene cores which have, for example, additional numbers of branches, arene planes, and/or extended bridge-head structures. For example, the central phenyl ring of a pentiptycene core may have an extended structure such as a central anthracene ring system. The synthesis of iptycenes and like molecules is described in, for example, Hart, "Iptycenes, Cuppendophanes and Cappedophanes," Pure and Applied Chemistry, 65(1):27-34 (1993); and Shahlia et al., "Synthesis of Supertriptycene and Two Related Iptycenes," Journal of Organic Chemistry, 56:6905-6912 (1991), the contents of which are incorporated herein by reference. In some embodiments, the iptycene core may be synthesized via a Diels-Alder reaction between an anthracene species and a benzyne species.

In some embodiments, the bridged bicyclic-based compound has a structure as in:

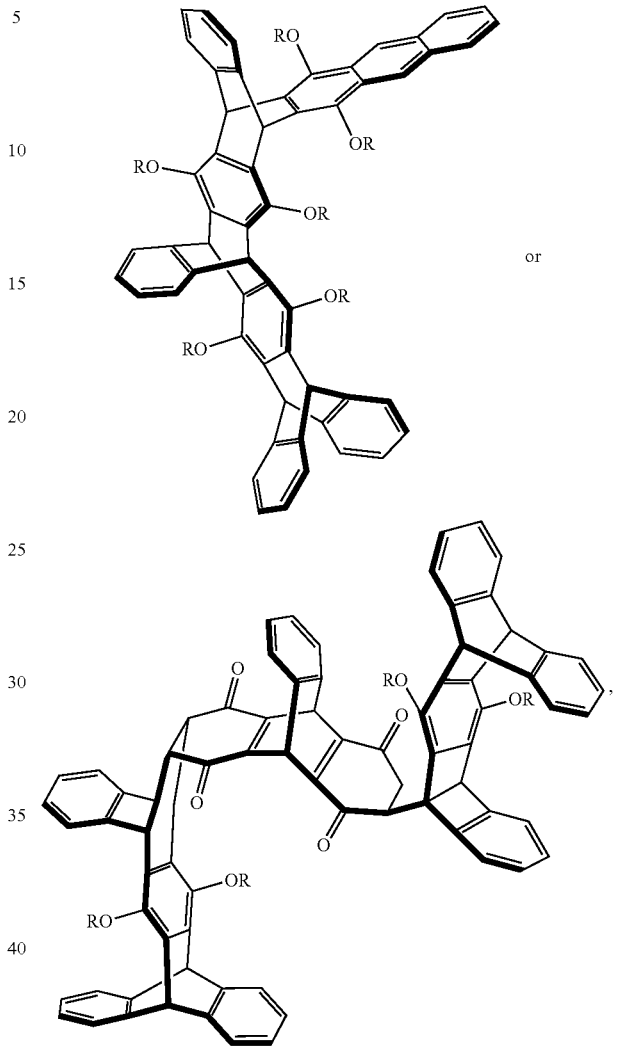

wherein each R can be the same or different and are hydrogen, halo, hydroxyl, amino, alkyl (e.g., $C_mH_{2m+1}$ where m is an integer and is at least 1), heteroalkyl, alkenyl, alkynyl, aryl, heteroaryl, heterocyclyl, or a carbonyl group, any of which is optionally substituted, or can be joined together to form an optionally substituted ring. For example, in some embodiments, each R may be the same or different and selected from the group consisting of $COC_mH_{2+1}$ and COR' where R' is selection from the group consisting of phenyl, (adaman-1-yl)methylene, and a polyolefin (e.g., —(CH$_2$)$_4$CHCH), and wherein m is 1-20. In some such embodiments, the bridged bicyclic-based compound is an oligoiptycene (e.g., a poly-iptycene having between 2-10 bicyclic cores).

In some embodiments, m is an integer and is at least 1. For example, in some embodiments, m is an integer in the range of from 1 to 20 (e.g., from 1 to 10, from 2 to 12, from 5 to 15, or from 10 to 20). Other ranges are also possible.

In some embodiments, the bridged bicyclic compound is a higher order polyiptcyene (e.g., an extended iptycene). In some such embodiments, the polyiptcyene may have a structure as in:

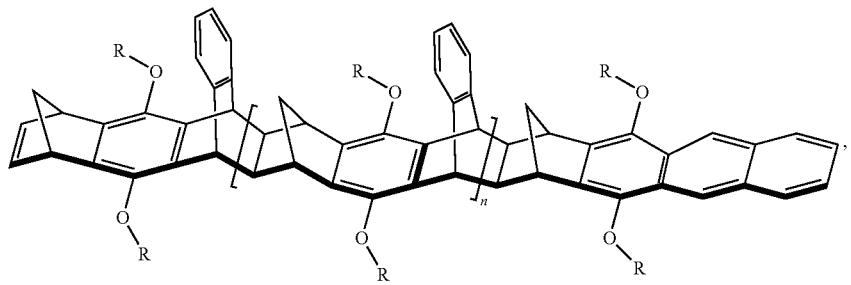

wherein each R can be the same or different and are hydrogen, halo, hydroxyl, amino, alkyl (e.g., $C_mH_{2+1}$ where m is an integer and is at least 1), heteroalkyl, alkenyl, alkynyl, aryl, heteroaryl, heterocyclyl, or a carbonyl group, any of which is optionally substituted, or can be joined together to form an optionally substituted ring, and n is an integer and is at least 1.

In some embodiments, n is an integer and is at least 1. In certain embodiments, n ranges between about 1 and 1000000. For example, in some cases, n is at least about 2, at least about 10, at least about 100, at least about 1,000, at least about 10,000, at least about 20,000, at least about 50,000 or at least about 75,000. In some embodiments, n is less than or equal to about 100,000, less than or equal to about 75,000, less than or equal to about 50,000, less than or equal to about 20,000, less than or equal to about 10,000, less than or equal to about 1,000, less than or equal to about 100, or less than or equal to about 10. Combinations of the above-referenced ranges are also possible (e.g., between about 2 and about 1,000, between about 1 and about 100,000, between about 10,000 and about 100,000). Other ranges are also possible.

In some embodiments, the bridged bicyclic compound comprises a molecular cage. In certain embodiments, the bridged bicyclic compound a first group attached to a first [2.2.2] bicyclic core and a second group attached to a second [2.2.2] bicyclic core, such that the bridged bicyclic compound comprises a molecular cage. In certain embodiments, a fixed distance between the first group and the second group is less than or equal to 10 Å, less than or equal to 9.5 Å, less than or equal to 9 Å, less than or equal to 8 Å, less than or equal to 7 Å, less than or equal to 5 Å, less than or equal to 4 Å, less than or equal to 3 Å, or less than or equal to 2 Å. In certain embodiments, the fixed distance between the first group and the second group is greater than or equal to 1 Å, greater than or equal to 2 Å, greater than or equal to 3 Å, greater than or equal to 4 Å, greater than or equal to 5 Å, greater than or equal to 7 Å, greater than or equal to 8 Å, greater than or equal to 9 Å, or greater than or equal to 9.5 Å. Combinations of the above-referenced ranges are also possible (e.g., greater than or equal to 1 Å and less than or equal to 10 Å). Other ranges are also possible. The fixed distance may be determined by measuring the distance between the atom of the first group closest to the atom of the second group, at their closest proximity taking into account variation in proximity that may occur with any movement/ orientation of the first and second groups relative to each other (e.g. rotation, vibration, and other movement normal and expected at room temperature). The distance between two atoms means as would be measured by those of ordinary skill in the art, generally involving the space taken by an atom being the extent of its electron cloud, as measured, for example, by the scattering of X-rays, or by measuring the density of a liquid. Alternatively, the equilibrium distances between atoms can be calculated from first principles using quantum chemical methods. FIG. 1A shows an illustrative embodiment of determining the fixed distance between the first group and the second group of an exemplary bridged bicyclic compound.

In some embodiments, the molecular cage has a largest cross-sectional dimension of less than or equal to 12 Å, less than or equal to 10 Å, less than or equal to 9.5 Å, less than or equal to 9 Å, less than or equal to 8 Å, less than or equal to 7 Å, or less than or equal to 5 Å. In certain embodiments, the molecular cage has a largest cross-sectional dimension of greater than or equal to 4 Å, greater than or equal to 5 Å, greater than or equal to 7 Å, greater than or equal to 8 Å, greater than or equal to 9 Å, or greater than or equal to 10 Å. Combinations of the above-referenced ranges are also possible (e.g., a largest cross-sectional dimension of greater than or equal to 4 Å and less than or equal to 12 Å). Other ranges are also possible. FIG. 1A shows an exemplary embodiment illustrating the largest-cross sectional dimension of an exemplary molecular cage.

In some embodiments, the bridged bicyclic-based compound has a particular number average molecular weight. In some embodiments, the number average molecular weight of the bridged bicyclic-based compound may be greater than or equal to 1000 Da, greater than or equal to 1500 Da, greater than or equal to 2500 Da, greater than or equal to 5000 Da, greater than or equal to 7500 Da, greater than or equal to 10000 Da, greater than or equal to 25000 Da, or greater than or equal to 50000 Da. In certain embodiments, the number average molecular weight of the bridged bicyclic-based compound may be less than or equal to 75000 Da, less than or equal to 50000 Da, less than or equal to 25000 Da, less than or equal to 10000 Da, less than or equal to 7500 Da, less than or equal to 5000 Da, less than or equal to 2500 Da, or less than or equal to 1500 Da. Combinations of the above-referenced ranges are also possible (e.g., greater than or equal to 1000 Da and less than or equal to 75000 Da). Other ranges are also possible.

An article or device comprising the bridged bicyclic-based compound may have a particular pore size. For example, in some embodiments, the article (e.g., a film comprising the bridged bicyclic-based compound) may have a pore size of at least 2 nm, at least 3 nm, at least 4 nm, at least 5 nm, or at least 10 nm. In certain embodiments, the device may have a pore size of less than or equal to 20 nm, less than or equal to 10 nm, less than or equal to 5 nm, less than or equal to 4 nm, or less than or equal to 3 nm. Combinations of the above-referenced ranges are also possible.

In some embodiments, an article or device comprising the bridged bicyclic-based compound may be used for separating gaseous compounds. For example, in some embodiments, the article or device may comprise a filter comprising the bridged bicyclic-based compound.

Some embodiments may provide the bridged bicyclic-based compound combined with, dispersed within, covalently bonded to, coated with, formed on, or otherwise associated with, one or more materials (e.g., small molecules, polymers, metals, metal complexes, etc.) to form a film or layer in solid state. For example, the bridged bicyclic compound may be combined with another material (e.g., a polymer) to form a film.

The term "alkyl" refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. The alkyl groups may be optionally substituted, as described more fully below. Examples of alkyl groups include, but are not limited to, methyl, ethyl, propyl, isopropyl, butyl, isobutyl, tert-butyl, 2-ethylhexyl, cyclopropyl, cyclobutyl, cyclopentyl, cyclohexyl, and the like. "Heteroalkyl" groups are alkyl groups wherein at least one atom is a heteroatom (e.g., oxygen, sulfur, nitrogen, phosphorus, etc.), with the remainder of the atoms being carbon atoms. Examples of heteroalkyl groups include, but are not limited to, alkoxy, poly(ethylene glycol)-, alkyl-substituted amino, tetrahydrofuranyl, piperidinyl, morpholinyl, etc. "Fluoroalkyl" groups are alkyl groups wherein at least one hydrogen is replaced with a fluoro group. In some cases, all hydrogen groups of an alkyl group are replaced with fluoro groups to form a fluoroalkyl group (e.g., $CF_3$).

The term "alkoxy" refers to —O-alkyl. A "fluoroalkoxy" group refers to —O— fluoroalkyl.

The terms "alkenyl" and "alkynyl" refer to unsaturated aliphatic groups analogous to the alkyl groups described above, but containing at least one double or triple bond respectively. The "heteroalkenyl" and "heteroalkynyl" refer to alkenyl and alkynyl groups as described herein in which one or more atoms is a heteroatom (e.g., oxygen, nitrogen, sulfur, and the like).

The term "aryl" refers to an aromatic carbocyclic group having a single ring (e.g., phenyl), multiple rings (e.g., biphenyl), or multiple fused rings in which at least one is aromatic (e.g., 1,2,3,4-tetrahydronaphthyl, naphthyl, anthryl, or phenanthryl), all optionally substituted. "Fluoroaryl" groups are aryl groups that are substituted with at least one fluoro group.

The terms "amine" and "amino" refer to both unsubstituted and substituted amines, e.g., a moiety that can be represented by the general formula: N(R')(R")(R''') wherein R', R", and R''' each independently represent a group permitted by the rules of valence.

The terms "acyl," "carboxyl group," or "carbonyl group" are recognized in the art and can include such moieties as can be represented by the general formula:

wherein W is H, OH, O-alkyl, O-alkenyl, or a salt thereof. Where W is O-alkyl, the formula represents an "ester." Where W is OH, the formula represents a "carboxylic acid." In general, where the oxygen atom of the above formula is replaced by sulfur, the formula represents a "thiolcarbonyl" group. Where W is a S-alkyl, the formula represents a "thiolester." Where W is SH, the formula represents a "thiolcarboxylic acid." On the other hand, where W is alkyl, aryl, or another carbon-containing substituent, the above formula represents a "ketone" group. Where W is hydrogen, the above formula represents an "aldehyde" group.

As used herein, the term "heterocycle" or "heterocyclyl" refers to a monocyclic or polycyclic heterocyclic ring that is either a saturated ring or an unsaturated non-aromatic ring. Typically, the heterocycle may include 3-membered to 14-membered rings. In some cases, 3-membered heterocycle can contain up to 3 heteroatoms, and a 4- to 14-membered heterocycle can contain from 1 to about 8 heteroatoms. Each heteroatom can be independently selected from nitrogen, which can be quaternized; oxygen; and sulfur, including sulfoxide and sulfone. The heterocycle may be attached via any heteroatom ring atom or carbon ring atom. Representative heterocycles include morpholinyl, thiomorpholinyl, pyrrolidinonyl, pyrrolidinyl, piperidinyl, piperazinyl, hydantoinyl, valerolactamyl, oxiranyl, oxetanyl, tetrahydrofuranyl, tetrahydropyranyl, tetrahydropyrindinyl, tetrahydropyrimidinyl, tetrahydrothiophenyl, tetrahydrothiopyranyl, and the like. A heteroatom may be substituted with a protecting group known to those of ordinary skill in the art, for example, the hydrogen on a nitrogen may be substituted with a tert-butoxycarbonyl group. Furthermore, the heterocyclyl may be optionally substituted with one or more substituents (including without limitation a halogen atom, an alkyl radical, or aryl radical). Only stable isomers of such substituted heterocyclic groups are contemplated in this definition.

As used herein, the term "heteroaromatic" or "heteroaryl" means a monocyclic or polycyclic heteroaromatic ring (or radical thereof) comprising carbon atom ring members and one or more heteroatom ring members (such as, for example, oxygen, sulfur or nitrogen). Typically, the heteroaromatic ring has from 5 to about 14 ring members in which at least 1 ring member is a heteroatom selected from oxygen, sulfur, and nitrogen. In another embodiment, the heteroaromatic ring is a 5 or 6 membered ring and may contain from 1 to about 4 heteroatoms. In another embodiment, the heteroaromatic ring system has a 7 to 14 ring members and may contain from 1 to about 7 heteroatoms. Representative heteroaryls include pyridyl, furyl, thienyl, pyrrolyl, oxazolyl, imidazolyl, indolizinyl, thiazolyl, isoxazolyl, pyrazolyl, isothiazolyl, pyridazinyl, pyrimidinyl, pyrazinyl, triazinyl, triazolyl, pyridinyl, thiadiazolyl, pyrazinyl, quinolyl, isoquniolyl, indazolyl, benzoxazolyl, benzofuryl, benzothiazolyl, indolizinyl, imidazopyridinyl, isothiazolyl, tetrazolyl, benzimidazolyl, benzoxazolyl, benzothiazolyl, benzothiadiazolyl, benzoxadiazolyl, carbazolyl, indolyl, tetrahydroindolyl, azaindolyl, imidazopyridyl, qunizaolinyl, purinyl, pyrrolo[2,3]pyrimidyl, pyrazolo[3,4]pyrimidyl, benzo(b)thienyl, and the like. These heteroaryl groups may be optionally substituted with one or more substituents.

Suitable substituents for various groups described herein, e.g., alkyl, alkoxy, alkyl sulfanyl, alkylamino, dialkylamino, alkylene, alkenyl, alkynyl, cycloalkyl, cycloalkenyl, heterocyclyl, aryl, aralkyl, heteroaryl, and heteroarylalkyl groups, include any substituent that will form a stable compound. Examples of substituents include alkyl, alkoxy, alkyl sulfanyl, alkylamino, dialkylamino, alkenyl, alkynyl, cycloalkyl, an cycloalkenyl, an heterocyclyl, an aryl, an heteroaryl, an aralkyl, an heteroaralkyl, a haloalkyl, —C(O)NR$^a$R$^b$, —NR$^c$C(O)R$^d$, halo, —OR$^c$, cyano, nitro, haloalkoxy, —C(O)R$^c$, —NR$^a$R$^b$, —SR$^c$, —C(O)OR$^c$, —OC(O)R$^c$, —NR$^c$C(O)NR$^a$R$^b$, OC(O)NR$^a$R$^b$, NR$^c$C(O)OR$^d$, S(O)$_p$R$^c$, or —S(O)$_p$NR$^a$R$^b$, wherein R$^a$ and R$^b$, for each occurrence are, independently, H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, or an optionally substituted heteroaralkyl; or $R^a$ and $R^b$ taken together with the nitrogen to which they are attached form optionally substituted heterocyclyl or optionally substituted heteroaryl; and $R^c$ and $R^d$ for each occurrence are, independently, H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, or an optionally substituted heteroaralkyl. In addition, alkyl, cycloalkyl, alkylene, heterocyclyl, and any saturated portion of a alkenyl, cycloalkenyl, alkynyl, aralkyl, or heteroaralkyl group, may also be substituted with =O, =S, or =$NR^c$.

Compounds described herein may also be in salt form. Illustrative salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, and pamoate (i.e., 1,1' methylene bis (2 hydroxy 3 naphthoate)) salts. In some cases, the salt may be formed from a compound described herein having an acidic functional group, such as a carboxylic acid functional group, and an inorganic or organic base. Suitable bases include, but are not limited to, hydroxides of alkali metals such as sodium, potassium, and lithium; hydroxides of alkaline earth metal such as calcium and magnesium; hydroxides of other metals, such as aluminum and zinc; ammonia, and organic amines, such as unsubstituted or hydroxy substituted mono, di, or trialkylamines; dicyclohexylamine; tributyl amine; pyridine; N methyl, N ethylamine; diethylamine; triethylamine; mono, bis, or tris (2 hydroxy lower alkyl amines), such as mono, bis, or tris (2 hydroxyethyl)-amine, 2 hydroxy tert butylamine, or tris (hydroxymethyl)methylamine, N, N, di lower alkyl N (hydroxy lower alkyl) amines, such as N,N dimethyl N (2 hydroxyethyl)-amine, or tri (2 hydroxyethyl)amine; N methyl D glucamine; and amino acids such as arginine, lysine, and the like.

In some cases, the salt may be prepared from a compound described herein having a basic functional group, such as an amino functional group, and an inorganic or organic acid. Suitable acids include, but are not limited to, hydrogen sulfate, citric acid, acetic acid, oxalic acid, hydrochloric acid, hydrogen bromide, hydrogen iodide, nitric acid, phosphoric acid, isonicotinic acid, lactic acid, salicylic acid, tartaric acid, ascorbic acid, succinic acid, maleic acid, besylic acid, fumaric acid, gluconic acid, glucaronic acid, saccharic acid, formic acid, benzoic acid, glutamic acid, methanesulfonic acid, ethanesulfonic acid, benzenesulfonic acid, and p-toluenesulfonic acid.

EXAMPLES

The following examples are intended to illustrate certain embodiments of the present invention, but do not exemplify the full scope of the invention.

An iterative reaction sequence was used to prepare extended iptycenes, wherein a Diels-Alder reactions and a subsequent aromatization afforded higher order iptycenes. Mechanochemical activation was used and suitable additives that efficiently promoted the reactions in solid state were identified. An efficient double Diels-Alder reaction allowed rapid access to functionalized iptycenes with molecular weights over 2000 Daltons.

Figure 1B:
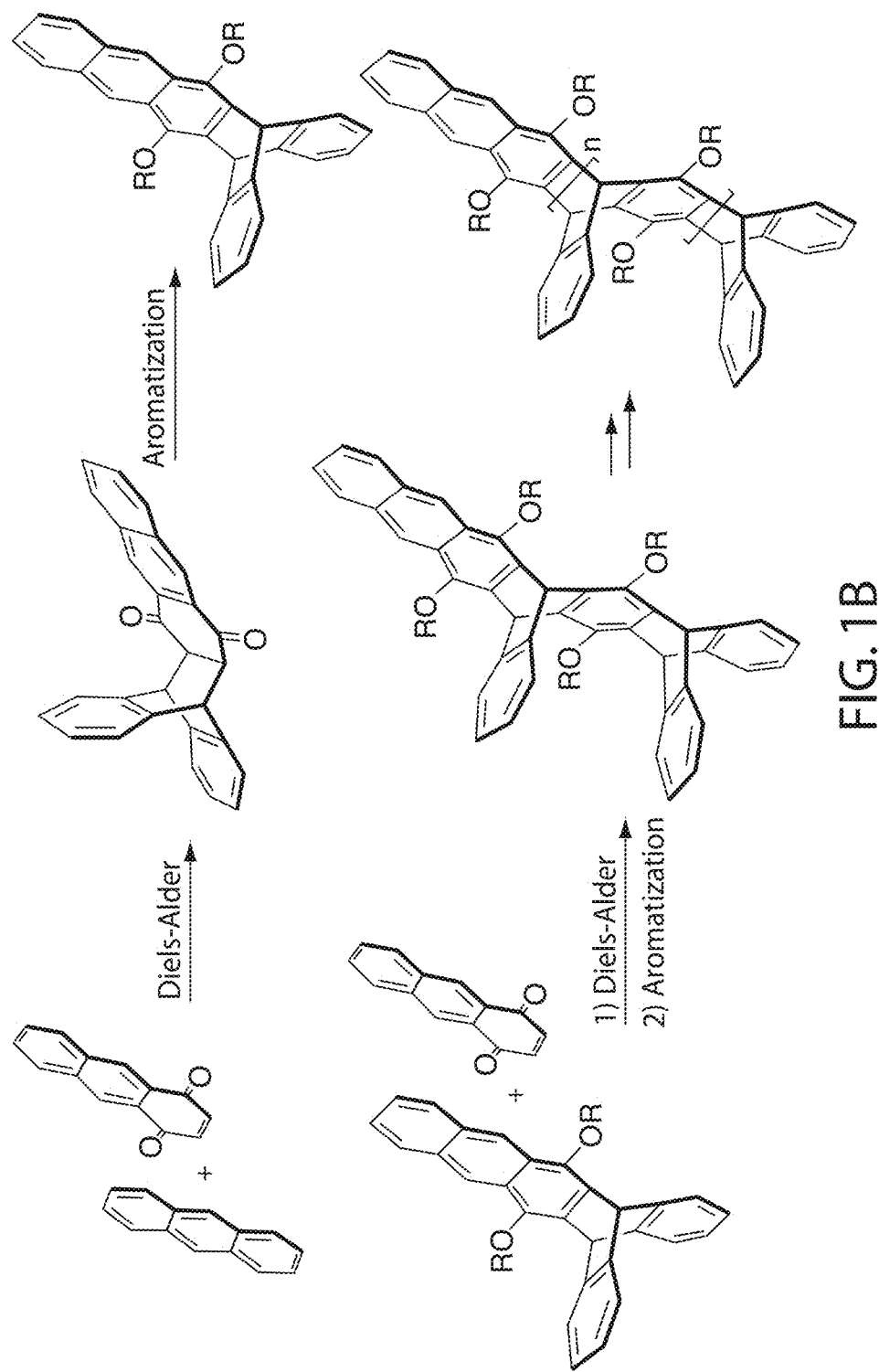
FIG. 1B is an exemplary reaction sequence for the synthesis of higher order iptycenes, according to one set of embodiments.

Similar to the original synthesis of triptycene, a Diels-Alder reaction was used to create the [2.2.2] bicyclic ring system. To achieve large, soluble and structurally well-defined iptycenes, a strategy for incorporation of functional groups with aromatization after each Diels-Alder reaction was employed. Iterative cycling of this process provided rapid access to functionalized extended iptycenes. These functional groups could be used to modify the resultant properties such as, for example, solubility. 1,4-Anthraquinone was used as a building block for this scheme, and its reaction with anthracene produced an enolizable 1,4-diketone that regenerated an anthracene derivative for the subsequent Diel-Alder reactions (FIG. 1B).

Figure 2:
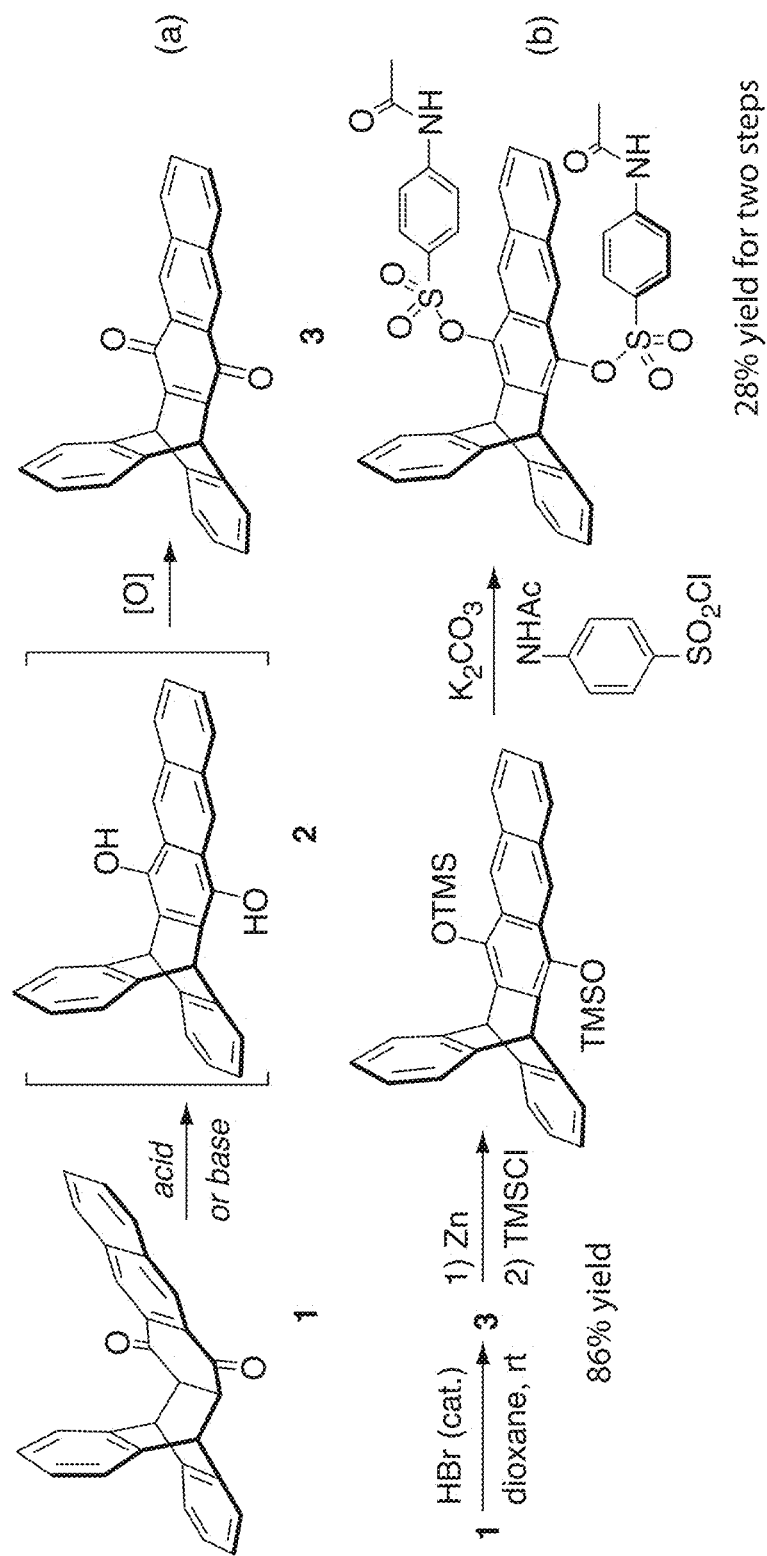
FIG. 2 is an exemplary synthesis of anthracene derivative, according to one set of embodiments.

Thermally activated Diels-Alder reactions often require long reaction time, which makes a long synthetic route generally impractical. Additionally at higher temperature retro-Diels-Alder reactions can be expected, which can also limit yields. Although strong Lewis acids, such as aluminum chloride ($AlCl_3$) may promote Diels-Alder reactions, these catalysts are generally not amenable when the structures contain sensitive functional groups. Secondly, anthracene-1,4-diol (2) produced by the enolization of 1 undergoes rapid air oxidation to form anthracene-1,4-dione (3) (FIG. 2, a). As a result, a synthesis with a coupled functionalization-aromatization step as illustrated in FIG. 1 was used. Alternative routes, avoiding this oxidation issue include silicon protection and then a deprotective sulfonylation sequence, which suffers from a limited yield (FIG. 2, b).

Figure 3:
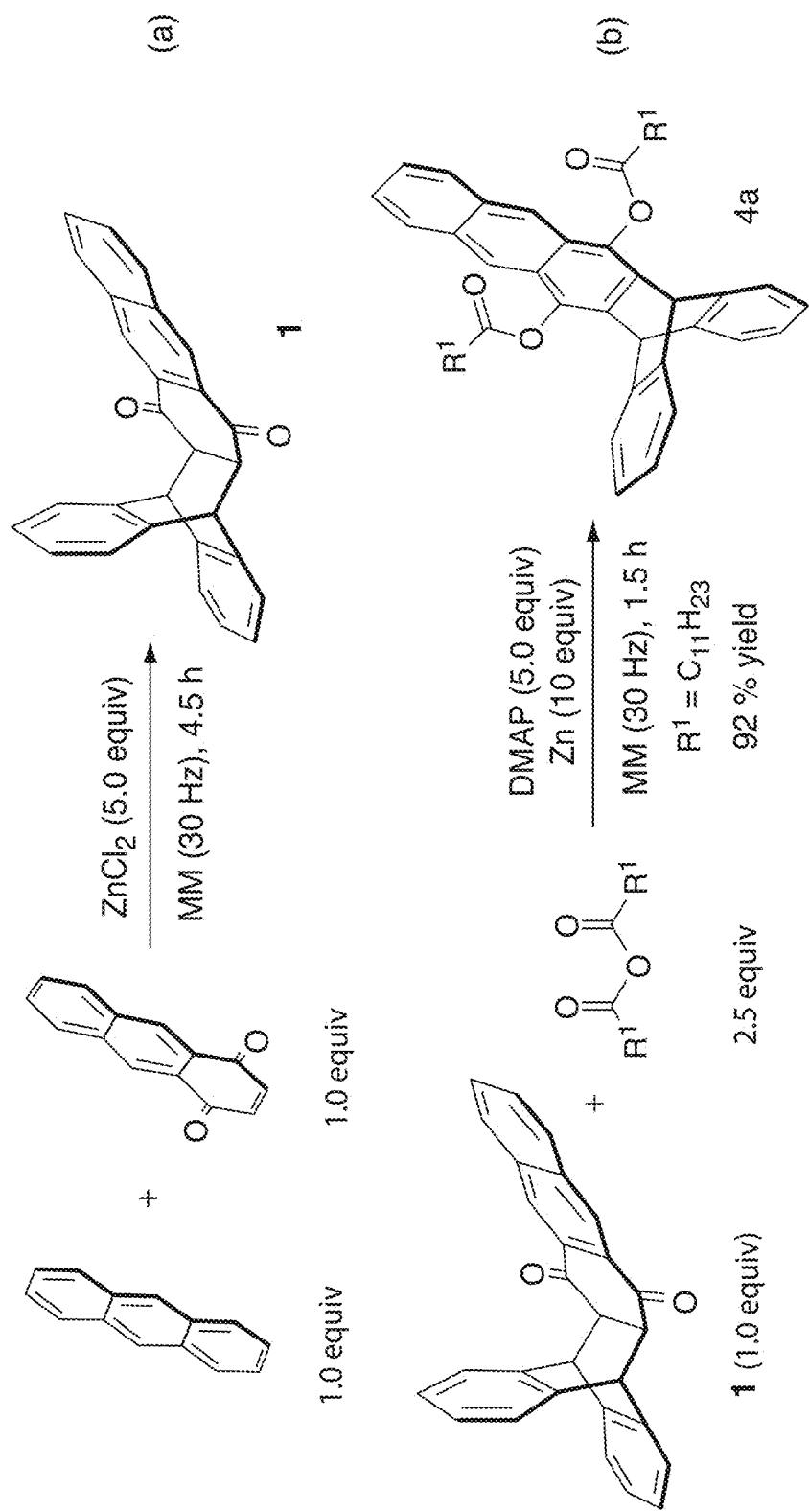
FIG. 3 is an exemplary reaction condition for each step of the iterative reaction sequence, according to one set of embodiments.

Various Lewis acids were screened with the aim to lower the LOMO energy of anthraquinone via coordination of the carbonyl groups with Lewis acid. It was quickly found that anhydrous $ZnCl_2$ was a suitable additive for the Diels-Alder reaction. A 5:1:1 ratio of $ZnCl_2$:anthracene:1,4-anthraquinone, gave full conversion of the reaction under vibration frequency of 30 Hz at room temperature in 4.5 h. Notably, column chromatography was not required to purify the product. The crude product was dissolved in dichloromethane and washed with 3N HCl to remove $ZnCl_2$. After concentration, the pure product was isolated in 85% yield by precipitation from methanol (FIG. 3, a).

Figure 4:
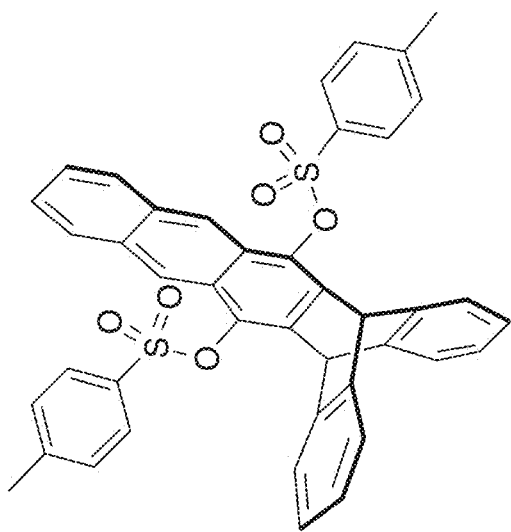
FIG. 4 shows anthracene derivatives prepared under mechanochemical condition, according to one set of embodiments.
Figure 4:
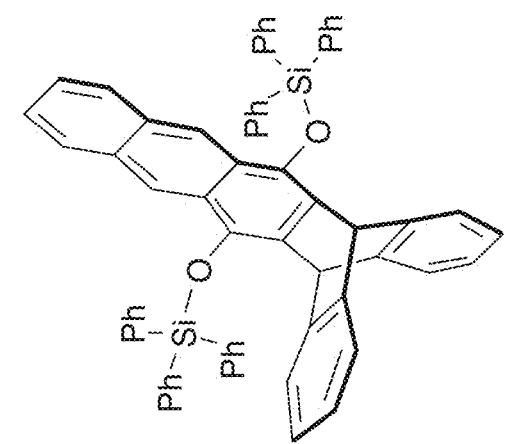
Figure 4:
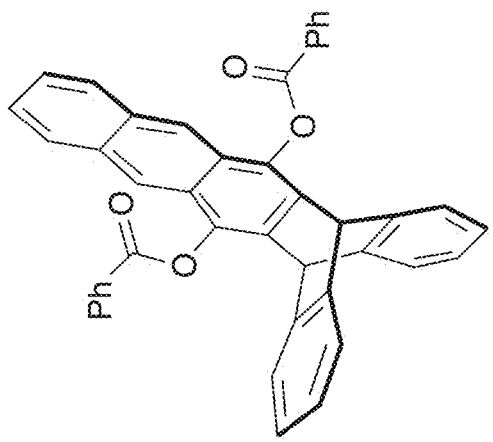

The conditions for the aromatization/functionalization step under ball-milling conditions using lauric anhydride as an acylating reagent and potassium carbonate as the base was then developed. It is noteworthy that the use of acid chlorides afforded generally lower yields as a result of reactions with the base. However, under these conditions oxidation is generally problematic and anthraquinone 3 (FIG. 2) was a major byproduct. The use of the N,N-dimethylpyridine (DMAP) as a base and zinc metal as an additive significantly increased the product yield. Without wishing to be bound by theory, the residue oxygen in the ball-milling vial could be consumed by the formation of zinc oxide. Furthermore, the electron rich metal surface may reduce 3, if formed, back to 2 for in-situ acylation. With the addition of zinc powder, the undesired oxidative pathway was suppressed. The crude product was dissolved in dichloromethane and filtered through a short pad of silica gel. After concentration, the pure product 4a was isolated in 92% yield by precipitation from methanol (FIG. 3, a). Benzoic anhydride, triphenylsilyl chloride, and tosyl chloride were also suitable electrophiles under the current condition, thereby giving access to a series of anthracene derivatives appended with various functional groups 4b-4d (FIG. 4).

To achieve extended iptycenes by using the iterative reaction sequence (FIG. 1), the Diels-Alder reaction between 4a-d and 1,4-anthraquinone was attempted. It was found that anthracene derivative 4a with an alkyl side chain gave a low yield of Diels-Alder product in presence of $ZnCl_2$, and no Diels-Alder product was observed with 4b, 4c, and 4d, which may be as a result of steric hindrance introduced by the bulky substituents. Steric effects can generally reduce diffusion rates, which can present significant difficulties in solid state reactions. It is also possible that competitive interaction of the $ZnCl_2$ with the ester can reduce the activation of 1,4-anthraquinone. To increase the mobility of the reactant in solid state and also enhance the activation of the dienophile, a Brønsted acid additive was employed. It is noteworthy that the symbiotic combination of Lewis acid and Brønsted acid may provide a higher acidity than that of each individual component to create unique catalytic properties.

Figure 5:
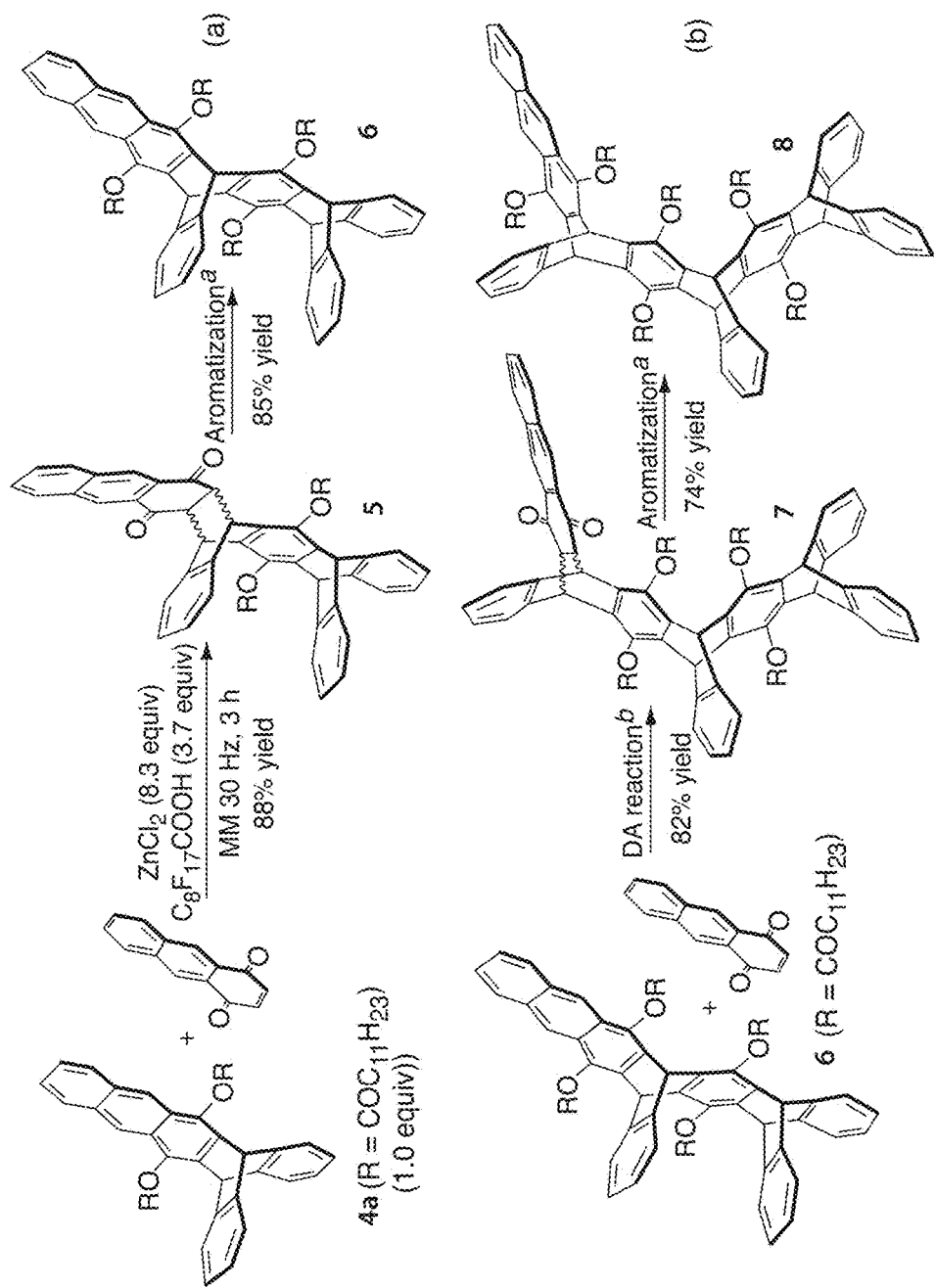
FIG. 5 shows an iterative reaction sequence for the synthesis of high order iptycene, according to one set of embodiments.

After a series of screening experiments, the addition of perfluorononanoic acid ($C_8F_{17}COOH$) allowed the desired transformation to proceed with high efficiency (FIG. 5, a). Repeating the designed iterative reaction sequence successfully produced the extended iptycene in good yield (FIG. 5, b). Without wishing to be bound by theory, as a result of the incorporated alkyl groups, the iptycenes synthesized through this method were highly soluble in common organic solvents, such as dichloromethane, chloroform, and tetrahydrofuran.

Figure 6:
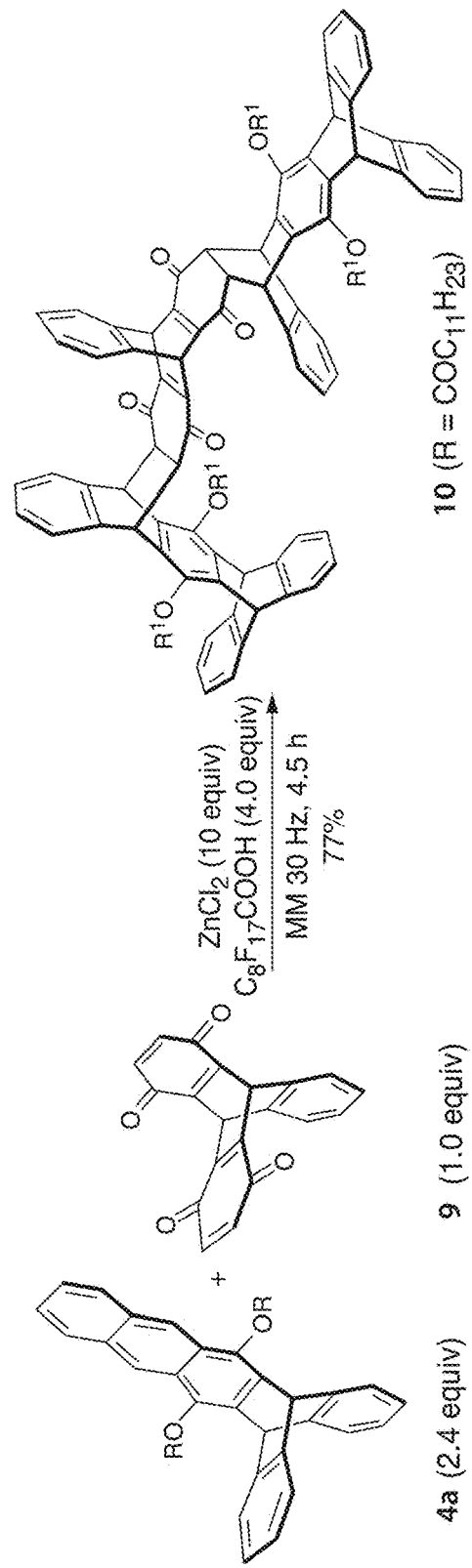
FIG. 6 shows the synthesis of high ordered iptycene through a double Diels-Alder reaction, according to one set of embodiments.
Figure 7:
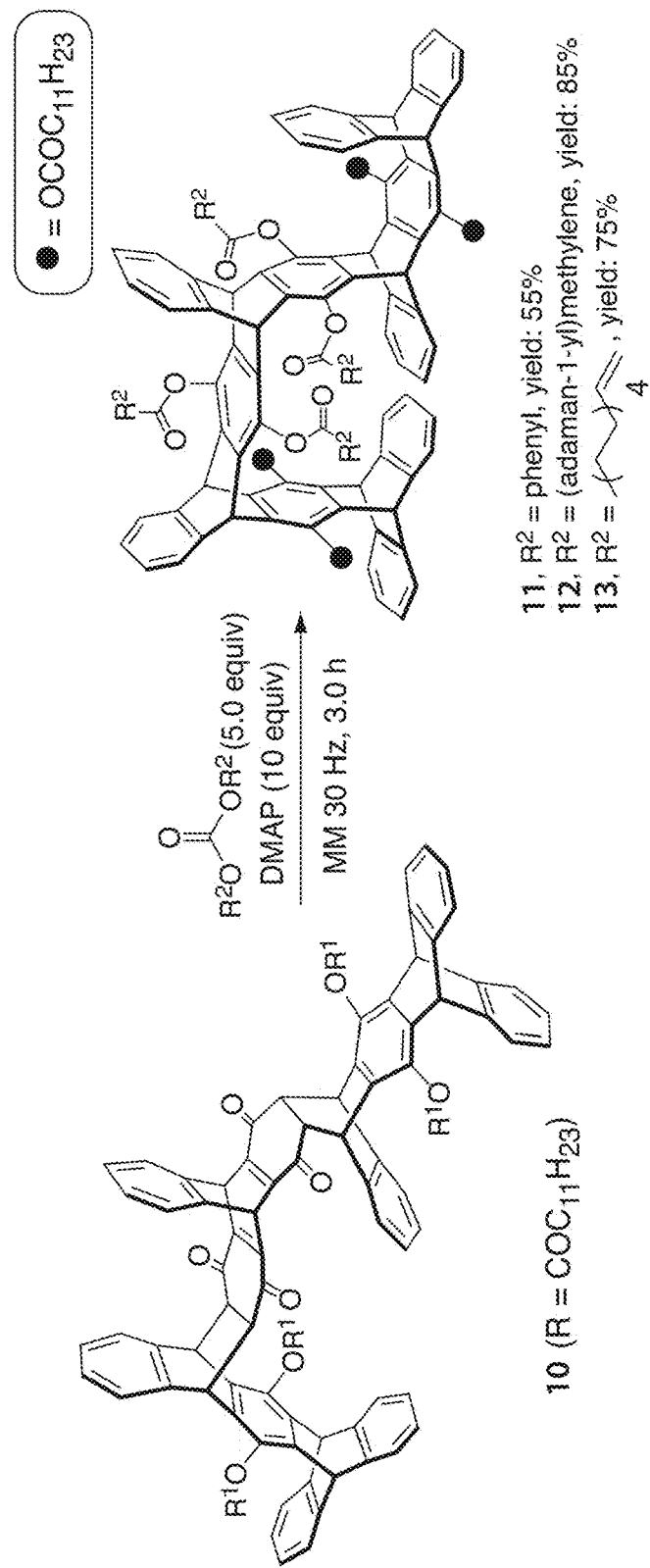
FIG. 7 shows the synthesis of molecular cage based on high order iptycene, according to one set of embodiments.

In order to accelerate the process to prepare larger iptycenes, the feasibility of a double Diels-Alder reaction by using triptycene diquinone as a bifunctionalized dienenophile was explored. By increasing the amount of $ZnCl_2$ and the additive $C_8F_{17}COOH$, the desired double Diels-Alder product was obtained in satisfactory yield (FIG. 6), demonstrating the high efficiency of mechanochemical reaction. Interestingly, although multiple stereoisomers can be generated, only one isomer was obtained in this reaction (FIG. 6). With the double Diels-Alder product 10 in hand, an iptycene-based molecular cage (defined by the cavity highlighted in blue in (FIG. 7) appended by various groups can be easily constructed through a four-fold esterification (FIG. 7).

Figure 8:
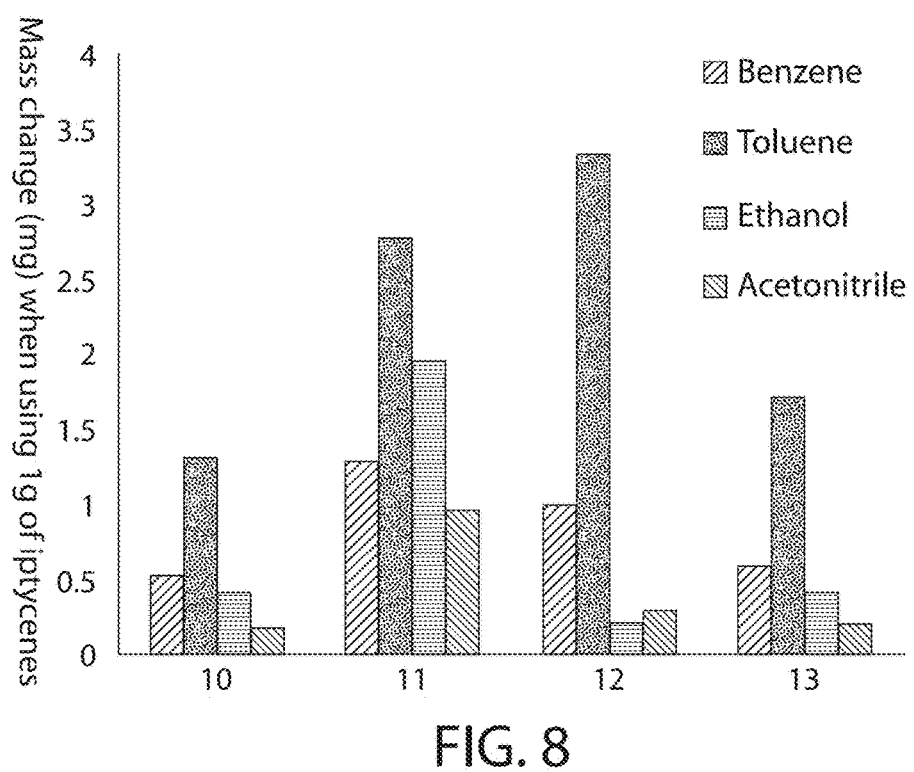
FIG. 8 is a plot of absorption properties of varies iptcyenes, according to one set of embodiments.

The absorption properties of 10-13 for selected molecules were tested by using a quartz crystal microbalance (QCM), and the results are summarized in FIG. 8. These molecules displayed good uptake upon exposure low concentrations (500 ppm) of organic vapors. Despite the fact that hydrogen boding and dipole interactions are strengthened in solid state structures, 10, 12, and 13 showed clear selectivity for the absorption of aromatic molecules over ethanol and acetonitrile. This latter effect may also be considered to be in part a result of the hydrophobic nature of these materials. Interestingly, the gas absorption selectivity could be tuned by incorporation of different side groups. For instance, 11 with a high arene composition showed a better uptake of all four kinds of gas vapor as compared to 10, whereas 12 containing adamantyl groups displayed significantly enhanced selectivity toward benzene and toluene. Such materials may be useful as filters or preconcentrators to selectively remove or detect organic vapors.

Synthesis of Porous Materials for Absorption of Organic Molecules

Polymeric materials often have large surface area because the connections between monomers decrease the amount of adaptable conformations such that the polymers align in a random way, thereby introducing void in solid state. In this regard, polyiptycene may be a useful candidate as gas absorption materials. Without wishing to be bound by theory, the noncompliant three-dimensional rigid structure may not only provide a relatively high surface area, but also increases the solubility of the polymer by preventing the self-aggregation. Furthermore, polyiptycene has a high arene composition and is generally capable of creating molecular cavitand by its concave backbone.

Figure 9:
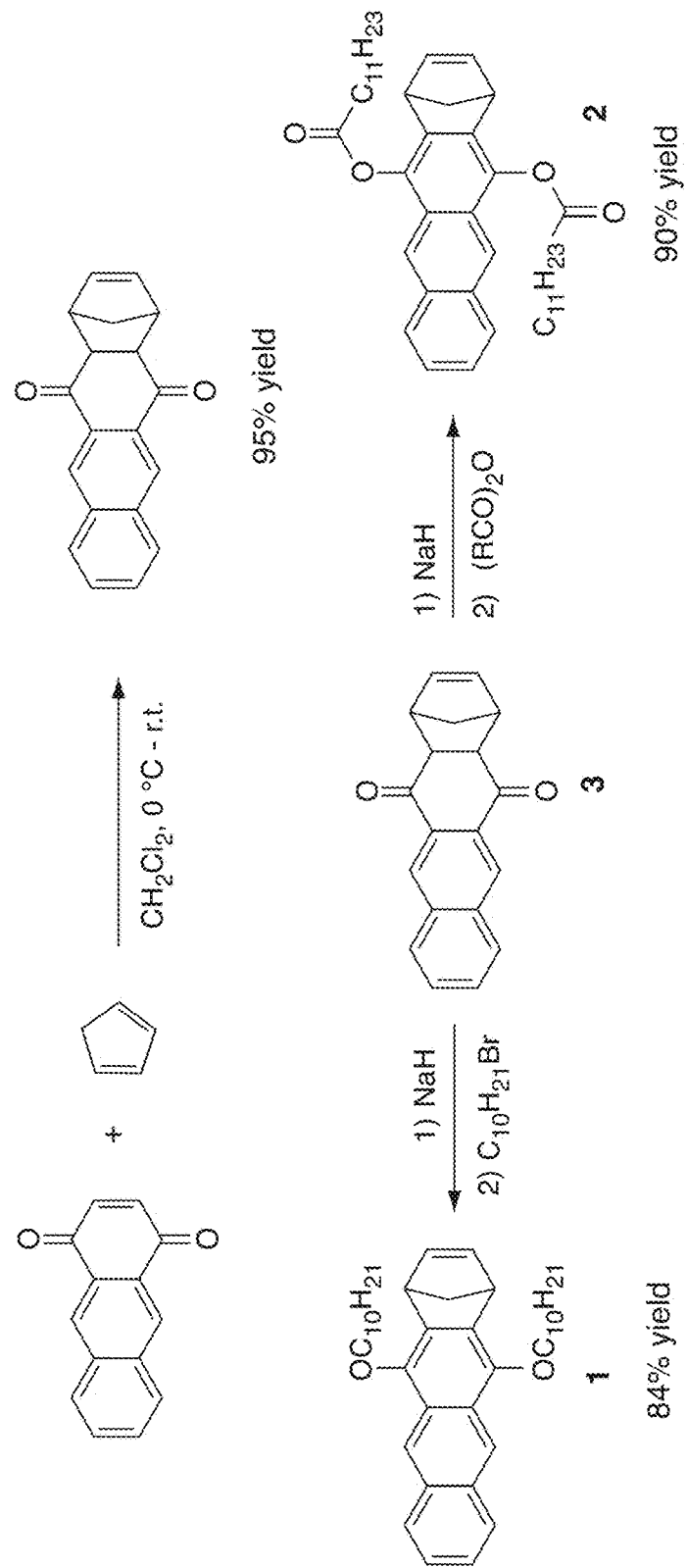
FIG. 9 shows the preparation of monomers for Diels-Alder polymerization, according to one set of embodiments.

To achieve an efficient preparation of polyiptycene, a Diels-Alder polymerization under solvent-free condition was developed. The monomers were synthesized and may be modified with various functional groups through alkylation or esterification (FIG. 9).

Figure 10:
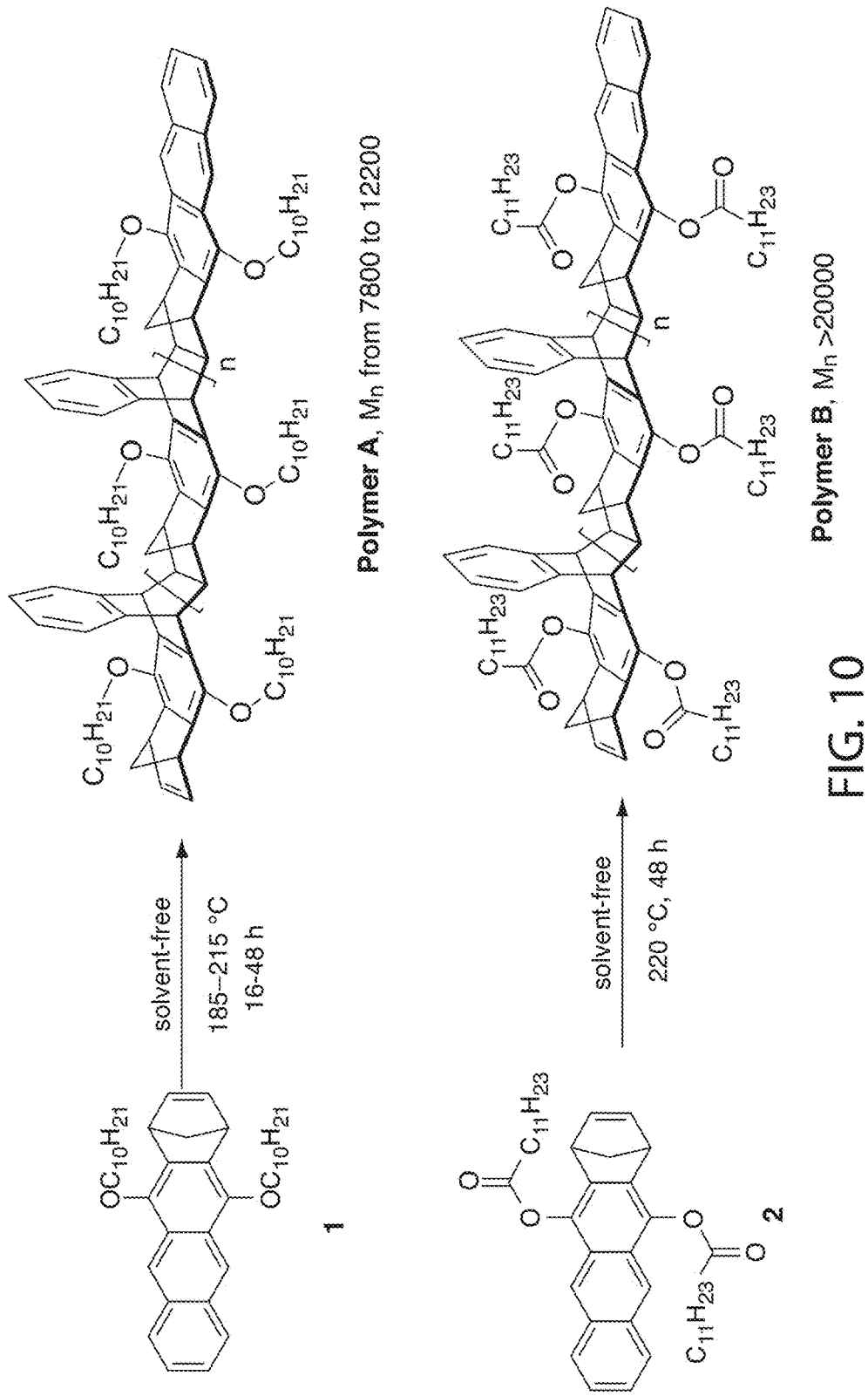
FIG. 10 shows the preparation of polyiptycene through solvent-free Diels-Alder reaction, according to one set of embodiments.
Figure 11:
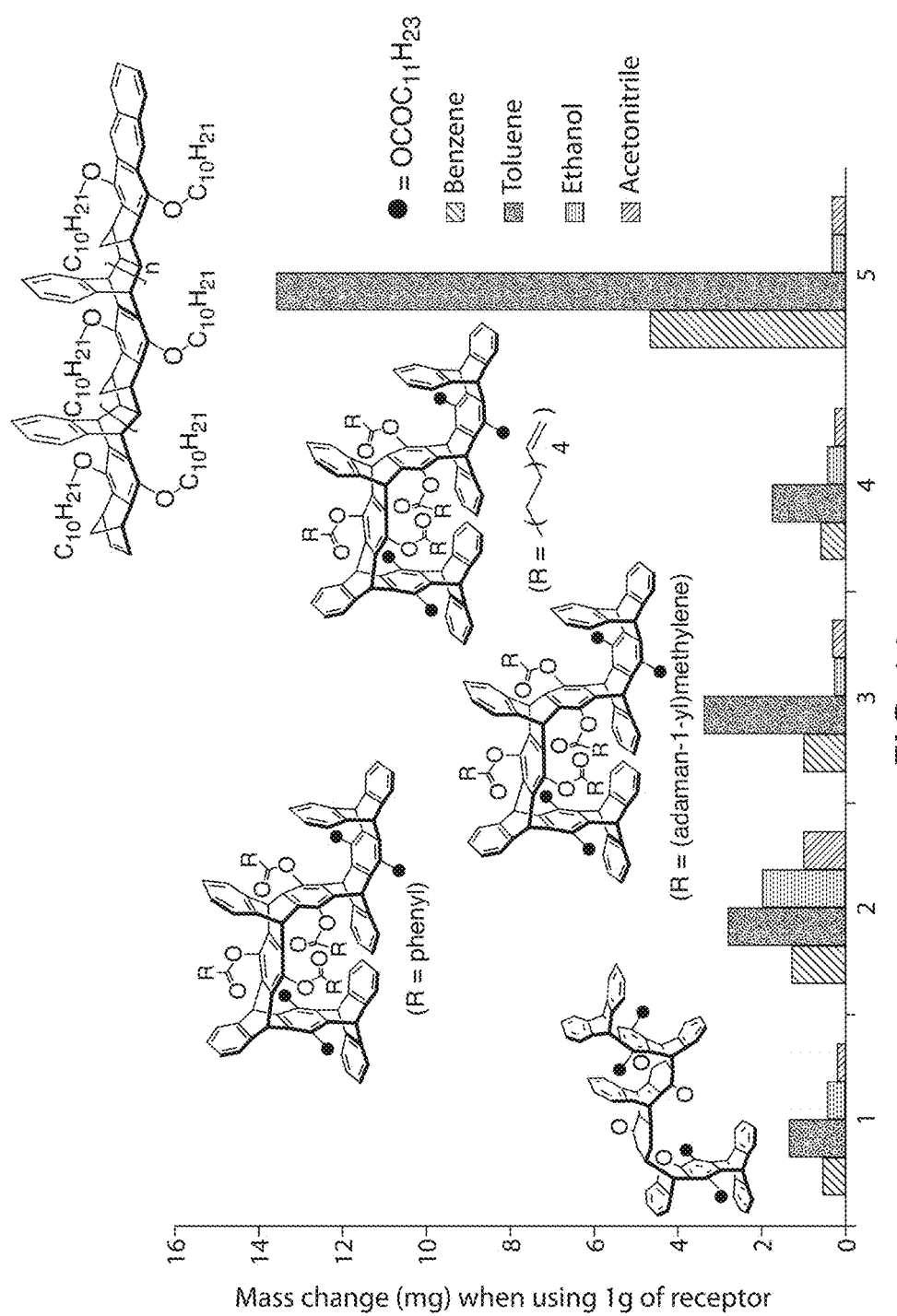
FIG. 11 shows the absorption abilities of iptycene-based materials, according to one set of embodiments.

Monomers with longer alkyl group were generally less crystalline and tended to have a low melting point, which may be important to obtain a high molecular weight (MW) polymer before solidification occurs under solvent-free condition. It is noteworthy that the polymerization was less efficient in solution and only oligomer was obtained when the reaction was carried out in 1,2-dichlorobenzene or diphenyl ether. The molecular weight of the polymer was partially controlled by reaction time, with longer reaction affording larger polymers. The polymerization of monomer 1 produced polymer (Polymer A) with MW between 7800 and 12200 Da. In contrast, polymer (Polymer B) with MW higher than 20000 Da was obtained by using monomer 2, which may be due to the electron-withdrawing property of the carbonyl group (FIG. 10). FIG. 11 shows the absorption abilities of iptycene-based materials.

Figure 12:
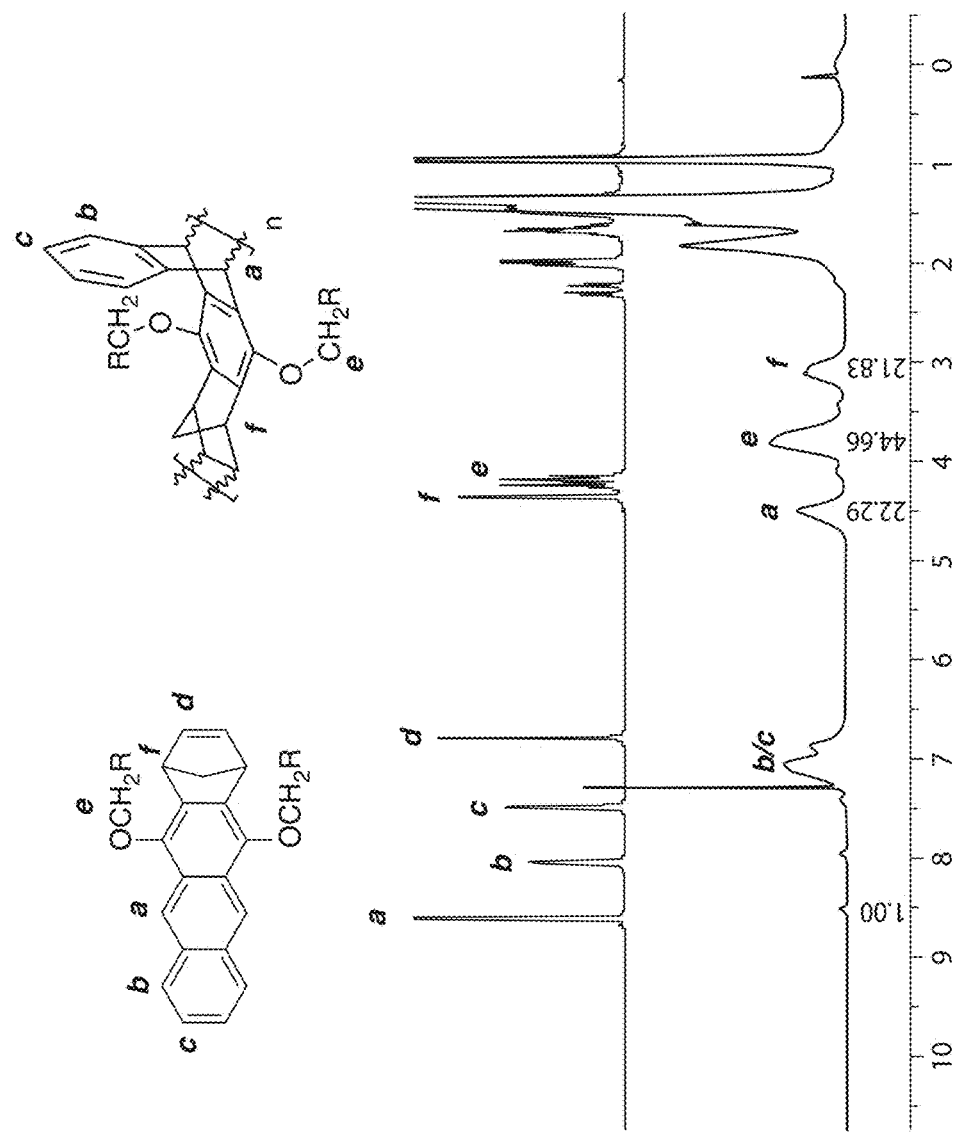
FIG. 12 shows the comparison of the $^1$H NMR of a monomer and a ladder-type polymer, according to one set of embodiments.
Figure 13:
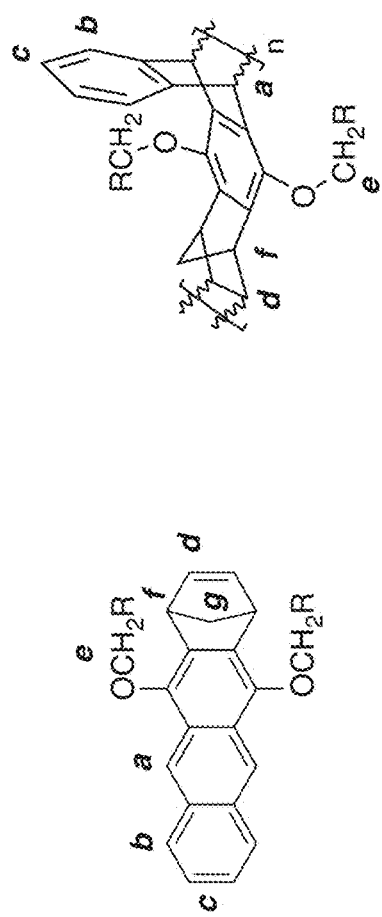
FIG. 13 shows the comparison of the $^{13}$C NMR of a monomer and a ladder-type polymer, according to one set of embodiments.
Figure 13:
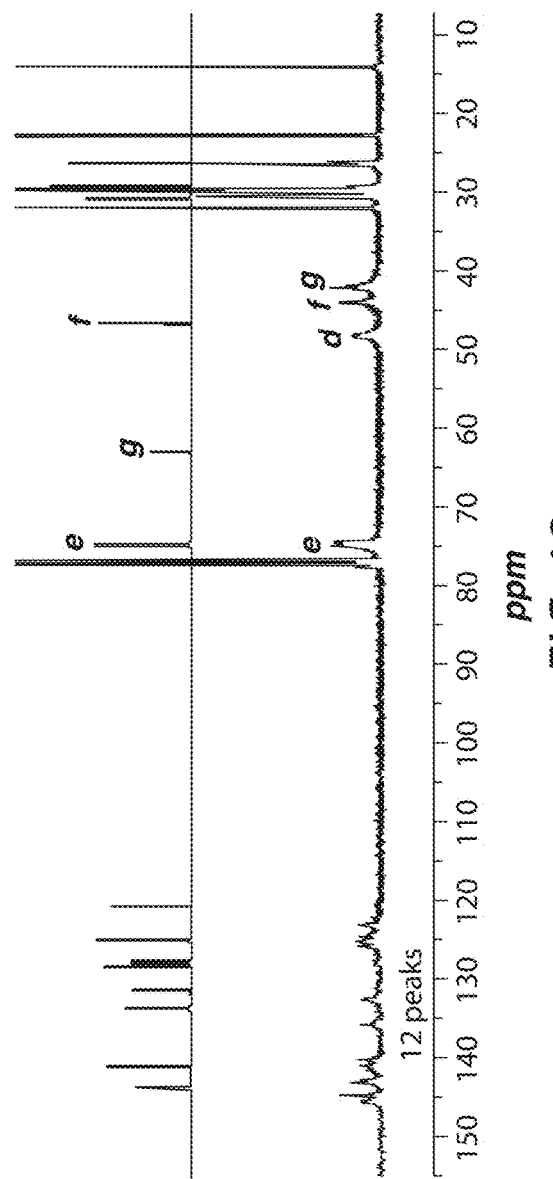
Figure 14:
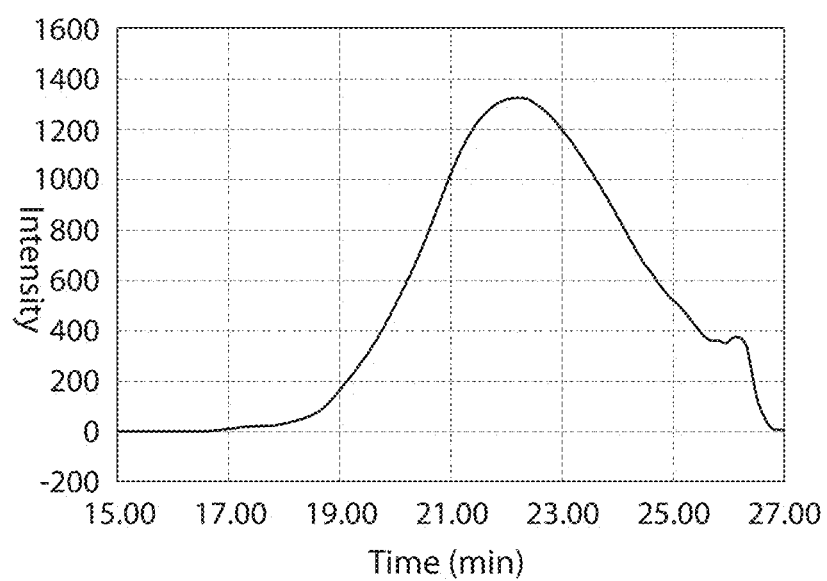
FIG. 14 is a plot of the gel permeation chromatography (GPC) trace of a ladder polymer, according to one set of embodiments.

FIG. 12 shows the comparison of the $^1H$ NMR of the monomer (FIG. 10, 1) and ladder-type polymer (FIG. 10, Polymer A). FIG. 13 shows the comparison of the $^{13}C$ NMR of the monomer (FIG. 10, 1) and ladder-type polymer (FIG. 10, Polymer A). FIG. 14 shows the gel permeation chromatography (GPC) trace of the ladder polymer.

$M_n$=12206 Da by NMR; 12606 Da by GPC, Đ=2.06

General Procedure for the Synthesis of Monomer 1 and 2.

To a solution of 3 (2.00 g, 7.29 mmol) in DMF (20 mL) was added NaH (874.1 mg, 60% wt %, 21.87 mmol, 3.0 equiv) under argon. The mixture was stirred for 2 min at room temperature before the addition of 1-bromodecane (4.03 g, 18.23 mmol, 2.5 equiv). The mixture was heated at 80° C. and stirred for 6 h before poured into a mixture of ice and water. The mixture was extracted with diethyl ether (3×120 mL) and the combined organic phase was washed with brine and dried over anhydrous $Na_2SO_4$. Evaporation of the solvent and the crude product was purified by silica gel chromatography using hexane/dichloromethane (5:1) as the eluent to give product 1 as a white solid (3.4 g, Yield: 84%). $^1H$ NMR (400 MHz, Chloroform-d) δ 8.61 (s, 2H), 8.05 (dd, J=6.4, 3.3 Hz, 2H), 7.48 (dd, J=6.5, 3.2 Hz, 2H), 6.79 (t, J=1.9 Hz, 2H), 4.36 (p, J=1.8 Hz, 2H), 4.20 (ddt, J=30.5, 9.4, 6.6 Hz, 4H), 2.31 (dt, J=7.7, 1.7 Hz, 1H), 2.22 (d, J=1.6 Hz, 1H), 2.04-1.93 (m, 4H), 1.73-1.59 (m, 4H), 1.56-1.27 (m, 24H), 1.01-0.90 (m, 6H). $^{13}C$ NMR (101 MHz, Chloroform-d) δ 143.71, 140.96, 133.62, 131.39, 128.39, 127.75, 125.07, 120.75, 74.78, 63.01, 46.70, 31.98, 30.63, 29.75, 29.68, 29.62, 29.43, 26.33, 22.76, 14.19.

Procedure for the Preparation of Ladder Polymer.

Mononer 1 was heated at 185-215° C. under argon for 24-48 h. The crude product was dissolved in a small amount of dichloromethane and was added dropwise to a stirring solution of methanol. The precipitation was filtered, washed with methanol, and dried under vacuum to give an off-white solid (yield>85%).

General Methods and Materials

Material:

All reactions were carried out under argon using standard Schlenk techniques unless otherwise noted. All solvents were of ACS reagent grade or better unless otherwise noted. Silica gel (40 μm) was purchased from SiliCycle Inc. All reagent grade materials were purchased from Alfa Aesar or Sigma-Aldrich and used without further purification. Mechanochemical syntheses were carried out in a conventional ball mill (Retsch, Mixer Mill 400).

NMR Spectroscopy:

$^1$H and $^{13}$C NMR spectra for all compounds were acquired in CDCl$_3$ on a Bruker Avance Spectrometer operating at 400 and 100 MHz for $^1$H NMR and $^{13}$C NMR, respectively). Chemical shifts (δ) are reported in parts per million (ppm) and referenced with TMS for $^1$H NMR and CDCl$_3$ for $^{13}$C NMR.

Infrared Spectroscopy:

Infrared spectra were recorded on a Thermo Scientific Nicolet 6700 Fourier Transform Infrared Spectrometer (FT-IR) using the attenuated total reflectance (ATR) technique on a Ge crystal.

Mass Spectrometry:

High-resolution mass spectra (HRMS) were obtained at the MIT Department of Chemistry Instrumentation Facility employing electrospray (ESI) as the ionization technique.

Quartz Crystal Microbalance (QCM) Measurements:

QCM measurements were performed on a Q-Sense E1 single-sensor micro-balance system, which was connected to a KIN-TEK gas generator system that was calibrated for each volatile organic analyte and was used to deliver the gaseous analyte diluted in nitrogen gas. The absorbing materials (10-13) were dissolved in benzene and were deposited on QCM sensor by dropcasting. The residue solvent was removed by putting the sensor under vacuum. The sensor was exposed to each analyte for 1 min with 2 min of nitrogen flow in between exposures to analyte.

Mechanochemical Synthesis of Cycloadduct (1) of anthrancene and 1,4-anthraquinone

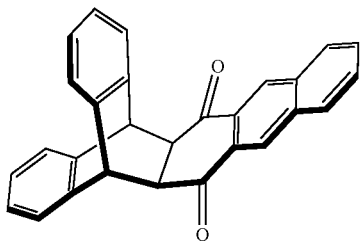

1

To a stainless steel vial (35 mL volume) was added anthrancene (1.03 g, 5.76 mmol), 1,4-anthraquinone (1.2 g, 1.0 equiv, 5.76 mmol) and ZnCl$_2$ (3.93 g, 5.0 equiv, 28.82 mmol) followed by one stainless milling ball (10 mm diameter). The tightly sealed vial was subjected to milling for 4.5 h at 30 Hz. Alter washing out the milling vial using H$_2$O (40 mL) and CH$_2$Cl$_2$ (100 mL). The aqueous phase was extracted with CH$_2$Cl$_2$ (100 mL) and the combined organic phase was collected and washed with 3N HCl and brine. After dried over Na$_2$SO$_4$, the solvent was evaporated to gave the crude product, which was dissolved in a small amount of CH$_2$Cl$_2$ and precipicited from cold MeOH. Vacuum filtration followed by washing with cold MeOH and drying gave cycloadduct 1 as a off-white solid (1.95 g, 5.04 mmol, yield: 87%). IR (ATR): 1619, 1458, 1291, 1266, 1192, 1039, 921, 829, 759, 747, 666, 641 cm$^{-1}$. $^1$H NMR (400 MHz, Chloroform-d) δ 8.45 (s, 2H), 7.97 (dd, J=6.2, 3.3 Hz, 2H), 7.64 (dt, J=6.3, 3.3 Hz, 2H), 7.49 (dd, J=5.4, 3.2 Hz, 2H), 7.23 (dd, J=1677, 5.4, 3.2 Hz, 2H), 7.16 (dd, J=5.4, 3.2 Hz, 2H), 6.81 (dd, J=5.4, 3.2 Hz, 2H), 5.12 (t, J=1.3 Hz, 2H), 3.49-3.46 (m, 2H). $^{13}$C NMR (101 MHz, Chloroform-d) δ 196.71, 142.25, 140.23, 135.03, 130.73, 129.87, 129.30, 128.72, 126.51, 126.31, 124.69, 123.89, 50.37, 49.22.[1] The charaterization data is consistent with that described in reference 1.

General Procedure for Mechanochemical Aromatization of 1, 5, or 7 with Various Anhydrides, Triphenylsilyl Chloride, and Tosyl Chloride.

To a stainless steel vial (35 mL volume) was added 1 (0.300 g, 0.78 mmol), lauric anhydride (0.743 mg, 2.5 equiv, 1.94 mmol), 4-dimethylaminopyridine (0.474 mg, 3.88 mmol, 5.0 equiv) and Zn (0.304 mg, 6.0 equiv, 4.68 mmol) followed by one stainless milling ball (10 mm diameter). The tightly sealed vial was subjected to milling for 1.5 h with a frequency of 30 Hz. After washing out the milling vial using CH$_2$Cl$_2$ (20 mL), the resulting CH$_2$Cl$_2$ solution was filtered through a short pad of silica gel and washed with CH$_2$Cl$_2$. The solvent was evaporated to gave the crude product, which was dissolved in a small amount of CH$_2$Cl$_2$ and precipitated from cold MeOH. Vacuum filtration followed by washing with cold MeOH and drying gave 4a as a white solid (539 mg, 0.72 mmol, yield: 92%).

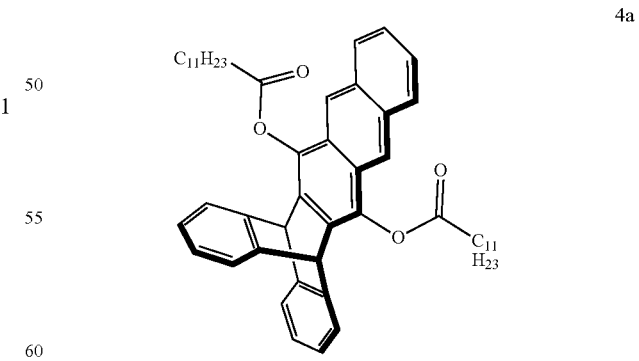

4a

M.P.: 89-92° C. IR (ATR): 2926, 2852, 1761, 1461, 1317, 1215, 1187, 1138, 1106, 998, 906, 876, 759, 751, 722, 640 cm$^{-1}$. $^1$H NMR (400 MHz, Chloroform-d) δ 8.29 (s, 2H), 7.96 (dt, J=6.4, 3.3 Hz, 2H), 7.46 (ddd, J=7.2, 5.9, 3.2 Hz, 6H), 7.11 (dd, J=5.4, 3.1 Hz, 4H), 5.54 (s, 2H), 3.02 (t, J=7.5

Hz, 4H), 2.12 (p, J=7.5 Hz, 4H), 1.79-1.66 (m, 4H), 1.64-1.25 (m, 28H), 1.01-0.87 (m, 6H). $^{13}$C NMR (101 MHz, Chloroform-d) δ 171.80, 143.13, 137.90, 131.74, 131.58, 128.27, 126.03, 125.88, 125.33, 124.30, 120.37, 48.55, 34.46, 31.98, 29.75, 29.72, 29.70, 29.57, 29.51, 29.42, 25.62, 22.74, 14.17. HRMS (ESI): calc for $C_{52}H_{63}O_4$ [M+NH$_4$]$^+$ 768.4986. found 768.4974.

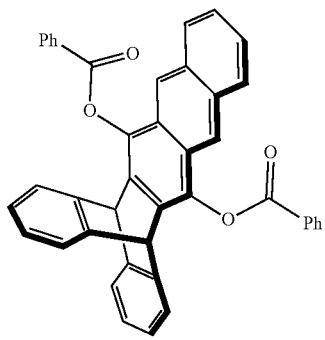

4b

4b. Yield: 85%. White solid. M.P.: 340-345° C. IR (ATR): 1741, 1463, 1450, 1252, 1239, 1204, 1176, 1139, 1114, 1096, 1075, 1050, 1025, 1002, 881, 855, 738, 707, 684, 640 cm$^{-1}$. $^1$H NMR (400 MHz, Chloroform-d) δ 8.52-8.46 (m, 4H), 8.27 (s, 2H), 7.83-7.73 (m, 4H), 7.66 (dd, J=8.3, 7.1 Hz, 4H), 7.37-7.28 (m, 6H), 7.00 (dd, J=5.4, 3.1 Hz, 4H), 5.53 (s, 2H). $^{13}$C NMR (101 MHz, Chloroform-d) δ 164.70, 143.23, 138.27, 134.15, 131.98, 131.85, 130.72, 129.25, 129.09, 128.30, 126.05, 125.88, 125.45, 124.41, 120.52, 48.53. HRMS (ESI): calc for $C_{42}H_{30}NO_4$ [M+NH$_4$]$^+$ 612.2169. found 612.2172.

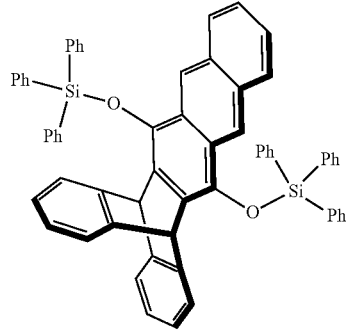

4c

4c: After precipitation from MeOH, 4c was further purified through column chromatography by using a mixture of hexane and dichloromethane as the eluent. Yield: 75%. White solid. M.P.: 279-282° C. IR (ATR): 1429, 1351, 1327, 1143, 1118, 1023, 880, 839, 820, 748, 739, 711, 699 cm$^{-1}$. $^1$H NMR (400 MHz, Chloroform-d) δ 8.06 (s, 2H), 7.71-7.63 (m, 12H), 7.45-7.35 (m, 6H), 7.29 (t, J=7.4 Hz, 12H), 7.15 (dt, J=6.4, 3.3 Hz, 2H), 7.10 (dt, J=6.6, 3.2 Hz, 2H), 6.68 (dd, J=5.4, 3.2 Hz, 4H), 6.58 (dd, J=5.4, 3.2 Hz, 4H), 5.65 (s, 2H). $^{13}$C NMR (101 MHz, Chloroform-d) δ 144.01, 139.81, 135.79, 133.85, 130.81, 130.48, 128.09, 128.03, 127.66, 126.48, 124.93, 124.79, 123.48, 122.16, 47.78. HRMS (ESI): calc for $C_{64}H_{47}O_2Si_2$ [M+H]$^+$ 903.3109. found 903.3118.

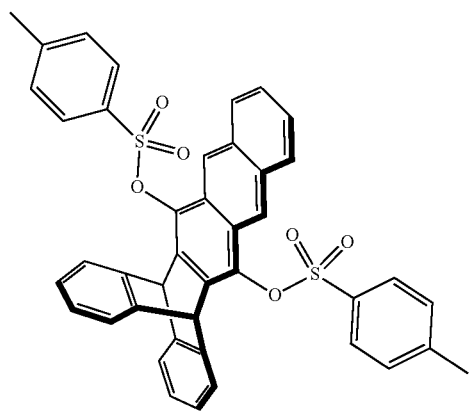

4d

4d: Yield: 79%. Light yellow solid. M.P.: 253-256° C. IR (ATR): 1385, 1366, 1303, 1190, 1173, 1087, 975, 891, 820, 810, 761, 749, 731, 706, 677, 668, 656, 642 cm$^{-1}$. $^1$H NMR (400 MHz, Chloroform-d) δ 7.85-7.81 (m, 4H), 7.64-7.59 (m, 6H), 7.39 (dt, J=6.4, 3.2 Hz, 2H), 7.35-7.31 (m, 2H), 7.27-7.23 (m, 4H), 7.14 (dd, J=5.5, 3.2 Hz, 4H), 6.22 (s, 2H), 2.39 (s, 6H). $^{13}$C NMR (101 MHz, Chloroform-d) δ 145.72, 143.26, 138.26, 135.10, 133.51, 131.15, 129.88, 128.63, 127.87, 126.03, 125.92, 124.95, 124.91, 48.69, 21.61. HRMS (ESI): calc for $C_{42}H_{34}NO_6S_2$ [M+NH$_4$]$^+$ 712.1822. found 712.1831.

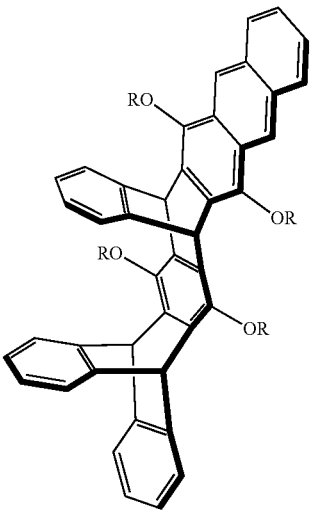

6

(R = COC$_{11}$H$_{23}$)

6: Light yellow solid. Yield: 85%. M.P.: 180-183° C. IR (ATR): 2923, 2853, 1765, 1464, 1316, 1199, 1133, 1106, 875, 751 cm$^{-1}$. $^1$H NMR (400 MHz, Chloroform-d) δ 8.09 (s, 2H), 7.80 (dd, J=6.4, 3.3 Hz, 2H), 7.33 (dt, J=6.4, 3.2 Hz, 2H), 7.20-7.12 (m, 6H), 6.91 (dd, J=5.4, 3.1 Hz, 2H), 6.83 (ddd, J=14.4, 5.4, 3.1 Hz, 4H), 5.41 (s, 2H), 5.21 (s, 2H), 2.87-2.74 (m, 8H), 1.97 (h, J=7.4 Hz, 8H), 1.65-1.12 (m, 64H), 0.88-0.75 (m, 12H). $^{13}$C NMR (101 MHz, Chloroform-d) δ 171.33, 171.08, 144.29, 144.15, 142.18, 138.79, 138.14, 137.08, 134.14, 131.74, 130.54, 128.25, 126.18, 125.89, 125.38, 125.35, 125.25, 124.49, 123.93, 123.86, 120.49, 49.06, 42.93, 34.41, 34.35, 31.98, 29.79, 29.76, 29.65, 29.58, 29.55, 29.43, 25.67, 25.57, 22.74, 14.16 (some of the aliphatic carbons are overlapped in $^{13}$C NMR). HRMS (ESI): calc for $C_{90}H_{114}NaO_8[M+Na]^+$ 1345.8406. found 1345.8428.

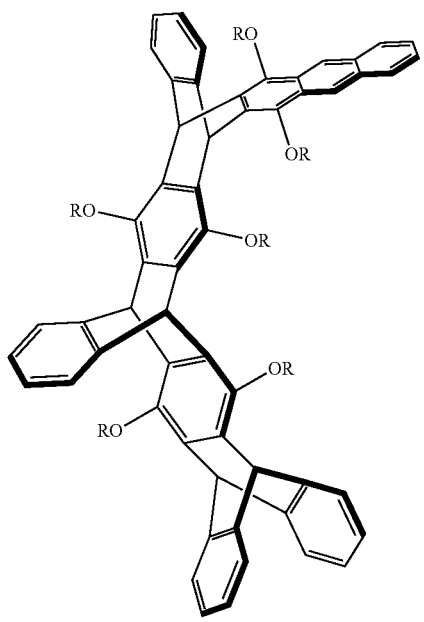

(R = COC$_{11}$H$_{23}$)

8: Light yellow solid. Yield: 73%. $^1$H NMR (400 MHz, Chloroform-d) δ 8.15 (s, 1H), 7.87 (dd, J=6.4, 3.3 Hz, 1H), 7.42 (dt, J=6.6, 3.2 Hz, 1H), 7.17 (dddd, J=30.7, 13.8, 5.4, 3.2 Hz, 4H), 7.03-6.95 (m, 1H), 6.88 (ddd, J=10.5, 5.4, 3.1 Hz, 2H), 6.75 (dd, J=5.4, 3.1 Hz, 1H), 5.42 (s, 1H), 5.32 (s, 1H), 5.21 (s, 1H), 2.98-2.72 (m, 6H), 2.02 (tt, J=12.0, 6.5 Hz, 7H), 1.71-1.24 (m, 34H), 0.92 (dq, J=7.0, 3.1 Hz, 10H). HRMS (ESI): calc for $C_{104}H_{126}NO_{10}[M+NH_4]^+$ 1914.2751. found 1914.2764.

Procedure for Mechanochemical Promoted Diels-Alder Reaction Between 4a or 6 and Anthraquinone.

To a stainless steel vial (35 mL volume) was added 4a (0.200 g, 0.26 mmol), anthraquinone (67 mg, 1.2 equiv, 0.32 mmol), ZnCl$_2$ (0.301 mg, 2.21 mmol, 8.3 equiv) and perfluorononanoic acid (156 mg, 0.985 mmol, 3.7 equiv) followed by one stainless milling ball (10 mm diameter). The tightly sealed vial was subjected to milling for 3 h with a frequency of 30 Hz. After washing out the milling vial using CH$_2$Cl$_2$ (20 mL), the resulting CH$_2$Cl$_2$ solution was filtered through a short pad of Al$_2$O$_3$ and washed with CH$_2$Cl$_2$. The solvent was evaporated to gave the crude product, which was dissolved in a small amount of CH$_2$Cl$_2$ and precipitated from cold MeOH. Vacuum filtration followed by washing with cold MeOH and drying gave 5 as a light yellow solid (240 mg, 0.25 mmol, yield: 94%). The product is a mixture of two stereoisomers.

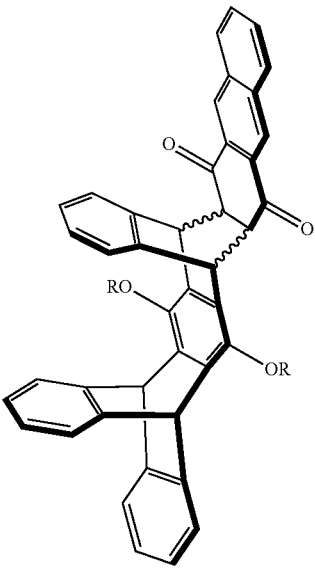

(R = COC$_{11}$H$_{23}$)

M.P.: 169-172° C. IR (ATR): 2926, 2854, 1760, 1681, 1620, 1459, 1299, 1265, 1191, 1135, 1102, 1036, 918, 758, 745 cm$^{-1}$. $^1$H NMR (The major isomer, 400 MHz, Chloroform-d) δ 8.31 (s, 2H), 7.85 (dd, J=6.2, 3.3 Hz, 2H), 7.52 (dt, J=6.4, 3.3 Hz, 2H), 7.24 (ddd, J=17.0, 5.4, 3.2 Hz, 4H), 7.05-6.95 (m, 2H), 6.94 (dd, J=5.4, 3.1 Hz, 2H), 6.86 (dd, J=5.4, 3.1 Hz, 2H), 6.71 (dd, J=5.5, 3.2 Hz, 2H), 5.35 (s, 2H), 4.98 (d, J=1.2 Hz, 2H), 3.29 (t, J=1.2 Hz, 2H), 2.92-2.84 (m, 4H), 2.00 (h, J=7.8 Hz, 4H), 1.63 (p, J=7.2 Hz, 4H), 1.55-1.15 (m, 28H), 0.88-0.76 (m, 6H). $^{13}$C NMR (The major isomer, 101 MHz, Chloroform-d) δ 195.86, 171.93, 144.41, 144.35, 139.68, 138.44, 137.06, 135.02, 132.81, 130.83, 129.83, 129.25, 128.67, 126.44, 125.50, 125.43, 124.92, 123.91, 123.87, 49.18, 48.78, 43.07, 34.38, 31.98, 29.78, 29.75, 29.69, 29.52, 29.50, 29.43, 25.66, 22.74, 14.16. HRMS (ESI): calc for $C_{66}H_{70}NaO_6$ [M+Na]$^+$ 981.5065. found 981.5066.

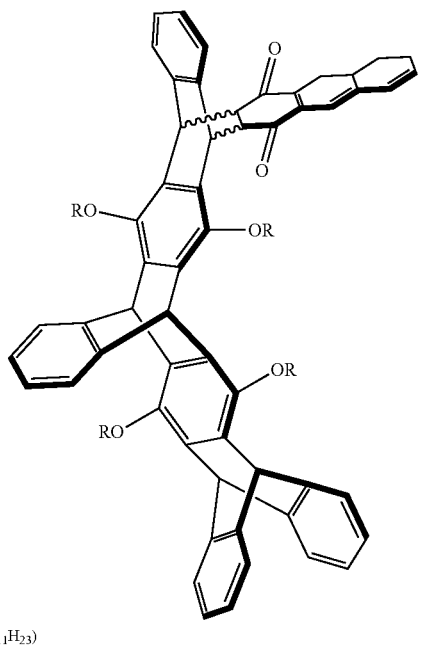

(R = COC$_{11}$H$_{23}$)

7: Light yellow solid. Yield: 82%. $^1$H NMR (400 MHz, Chloroform-d) δ 8.39 (s, 2H), 7.93 (dd, J=6.2, 3.3 Hz, 2H), 7.60 (dt, J=6.4, 3.3 Hz, 2H), 7.28 (s, 2H), 7.16 (dd, J=5.4, 3.2 Hz, 2H), 7.04 (dd, J=5.4, 3.2 Hz, 2H), 6.93 (dd, J=5.4, 3.1 Hz, 4H), 6.87 (dd, J=5.4, 3.1 Hz, 2H), 6.78 (dd, J=5.5, 3.1 Hz, 2H), 5.45 (s, 2H), 5.30 (s, 2H), 4.98 (t, J=1.2 Hz, 2H), 3.42 (t, J=1.2 Hz, 2H), 2.94-2.82 (m, 8H), 2.08 (p, J=7.5 Hz, 8H), 1.68 (q, J=7.4 Hz, 8H), 1.64-1.21 (m, 56H), 0.91 (h, J=5.1, 4.4 Hz, 12H). HRMS (ESI): calc for $C_{104}H_{126}NO_{10}$ $[M+NH_4]^+$ 1549.9376. found 1549.9342.

Procedure for Mechanochemical Promoted Double Diels-Alder Reaction Between 4a and 9.

To a $ZrO_2$ vial (35 mL volume) was added 9 (0.040 g, 0.126 mmol), 4a (237 mg, 2.5 equiv, 0.316 mmol), $ZnCl_2$ (0.172 mg, 1.26 mmol, 10 equiv) and perfluorononanoic acid (235 mg, 0.505 mmol, 4.0 equiv) followed by one $ZrO_2$ milling ball (10 mm diameter). The tightly sealed vial was subjected to milling for 4.5 h with a frequency of 30 Hz. After washing out the milling vial using $CH_2Cl_2$ (20 mL), the resulting $CH_2Cl_2$ solution was filtered through a short pad of silica gel and washed with $CH_2Cl_2$. The solvent was evaporated to gave the crude product, which was purified by silica gel column chromatography by using a mixture of hexane and ethyl acetate as the eluent to give 10 as an off-white solid, which was washed with cold methanol to give pure product (177 mg, 0.097 mmol, yield: 77%).

10

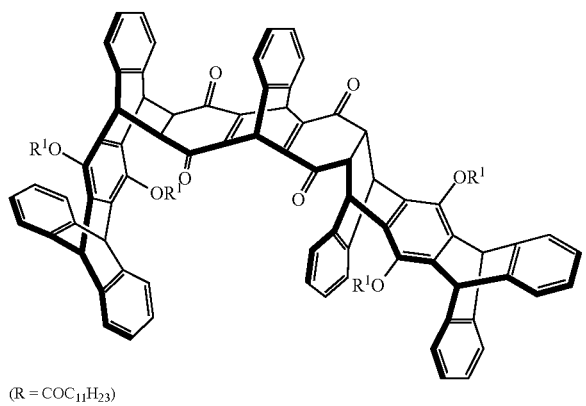

(R = $COC_{11}H_{23}$)

10: M.P.: 217-220° C. IR (ATR): 2925, 2854, 1768, 1671, 1560, 1459, 1366, 1298, 1253, 1191, 1136, 1107, 996, 968, 781, 759, 748 cm$^{-1}$. $^1$H NMR (400 MHz, Chloroform-d) δ 7.30-7.12 (m, 8H), 6.99-6.87 (m, 6H), 6.82 (td, J=5.3, 3.0 Hz, 4H), 6.79-6.74 (m, 2H), 6.67 (dd, J=5.3, 3.2 Hz, 2H), 6.49 (dt, J=6.0, 3.2 Hz, 4H), 6.10 (dd, J=5.5, 3.1 Hz, 2H), 5.34 (s, 2H), 5.28 (s, 2H), 5.25 (s, 2H), 4.40 (d, J=1.3 Hz, 2H), 4.36 (d, J=1.3 Hz, 2H), 2.87-2.74 (m, 12H), 2.02-1.87 (m, 8H), 1.64-1.15 (m, 60H), 0.83 (td, J=6.9, 2.3 Hz, 12H). $^{13}$C NMR (101 MHz, Chloroform-d) δ 192.60, 192.35, 171.78, 171.70, 155.05, 144.27, 144.20, 144.15, 140.81, 138.44, 138.38, 138.30, 137.42, 137.36, 137.22, 131.69, 131.43, 126.54, 125.58, 125.53, 125.45, 125.41, 124.80, 124.50, 123.93, 123.86, 123.68, 49.72, 49.17, 48.77, 44.85, 44.62, 42.25, 34.32, 34.25, 32.02, 29.80, 29.77, 29.76, 29.72, 29.67, 29.53, 29.47, 25.64, 25.57, 22.78, 14.21 (some of the signals are overlapped in $^{13}$C NMR). HRMS (ESI): calc for $C_{124}H_{138}NO_{12}$ $[M+NH_4]^+$ 1834.0247. found 1834.0222.

General Procedure for Mechanochemical Aromatization of 10 with Various Anhydrides.

To a stainless steel vial (35 mL volume) was added 10 (0.070 g, 0.0385 mmol), 1-adamantaneacetic anhydride (0.074 mg, 5.0 equiv, 0.192 mmol), 4-dimethylaminopyridine (0.047 mg, 0.385 mmol, 10 equiv) and Zn (0.015 mg, 6.0 equiv, 0.231 mmol) followed by one stainless milling ball (10 mm diameter). The tightly sealed vial was subjected to milling for 3.0 h with a frequency of 30 Hz. After washing out the milling vial using $CH_2Cl_2$ (20 mL), the resulting $CH_2Cl_2$ solution was filtered through a short pad of silica gel and washed with $CH_2Cl_2$. The solvent was evaporated to gave 12 as a white solid (82 mg, 0.0325 mmol, yield: 85%).

12

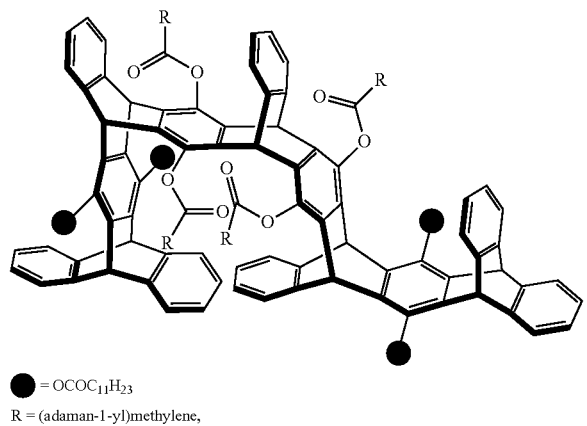

● = $OCOC_{11}H_{23}$
R = (adaman-1-yl)methylene,

M.P.: 157-160° C. IR (ATR): 2923, 2851, 1766, 1461, 1242, 1112, 1095, 748 cm$^{-1}$. $^1$H NMR (400 MHz, Chloroform-d) δ 7.09 (ddd, J=17.7, 5.4, 3.2 Hz, 8H), 6.88 (ddt, J=12.7, 5.3, 3.2 Hz, 6H), 6.82-6.64 (m, 14H), 5.22 (s, 2H), 5.17 (s, 2H), 5.16 (s, 2H), 5.11 (s, 2H), 5.08 (s, 2H), 2.67 (ddt, J=12.2, 8.3, 5.1 Hz, 8H), 2.55-2.36 (m, 8H), 2.08 (d, J=13.0 Hz, 12H), 2.01-1.14 (m, 120H), 0.83 (dt, J=7.1, 3.9 Hz, 12H). $^{13}$C NMR (101 MHz, Chloroform-d) δ 170.97, 170.90, 168.24, 168.19, 144.49, 144.44, 144.20, 144.16, 143.73, 143.65, 143.45, 138.66, 138.57, 136.37, 136.27, 135.78, 135.74, 135.73, 135.57, 135.53, 135.33, 125.34, 125.28, 125.22, 125.19, 123.90, 123.83, 123.72, 49.07, 48.85, 48.09, 47.89, 43.63, 43.60, 43.47, 42.66, 42.54, 36.86, 36.79, 34.42, 34.25, 33.10, 32.91, 31.98, 29.76, 29.73, 29.64, 29.60, 29.56, 29.50, 29.43, 29.42, 28.65, 28.61, 25.66, 25.59, 22.76, 14.18 (some of the signals are overlapped in $^{13}$C NMR). HRMS (ESI): calc m/z for $C_{172}H_{206}N_2O_{162}$ $[M+2NH_4]^{2+}$ 1278.2695. found 1278.2680.

11

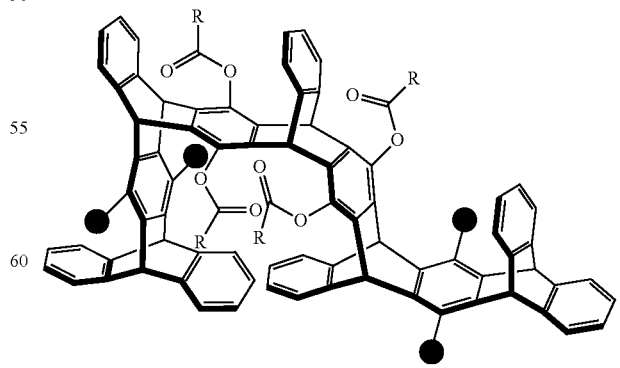

● = $OCOC_{11}H_{23}$
R = COPh

11: Off-white solid. Yield: 55%. M.P.: 155-158° C. IR (ATR): 2926, 2853, 1748, 1461, 1269, 1231, 1216, 1177, 1135, 1103, 1082, 1063, 1026, 750, 706, cm$^{-1}$. $^1$H NMR (400 MHz, Chloroform-d) δ 8.23-8.14 (m, 4H), 8.08 (d, J=7.6 Hz, 4H), 7.59 (t, J=7.4 Hz, 2H), 7.50 (t, J=7.4 Hz, 2H), 7.40 (t, J=7.7 Hz, 4H), 7.26 (t, J=7.6 Hz, 4H), 7.15-6.88 (m, 14H), 6.87-6.63 (m, 14H), 5.30 (s, 2H), 5.15 (s, 2H), 5.11 (s, 2H), 5.06 (s, 2H), 5.03 (s, 2H), 2.32-2.06 (m, 8H), 1.53 (d, J=12.0 Hz, 12H), 1.36-1.01 (m, 60H), 0.84 (dd, J=6.9, 3.5 Hz, 12H). $^{13}$C NMR (101 MHz, Chloroform-d) δ 170.95, 170.90, 163.70, 163.53, 144.44, 144.22, 144.21, 143.64, 143.52, 143.41, 138.97, 138.93, 138.63, 138.54, 136.32, 136.25, 136.14, 135.97, 135.48, 135.19, 133.52, 130.28, 130.17, 129.22, 128.91, 128.72, 128.60, 125.416, 125.391, 125.19, 124.25, 124.17, 124.04, 123.87, 123.82, 123.70, 48.83, 43.69, 43.58, 33.91, 33.86, 32.01, 29.76, 29.68, 29.45, 29.34, 29.31, 22.78, 14.21 (some of the signals are overlapped in $^{13}$C NMR). HRMS (ESI): calc m/z for $C_{152}H_{158}N_2O_{16}$ $[M+2NH_4]^{2+}$ 1134.0817. found 1134.0837.

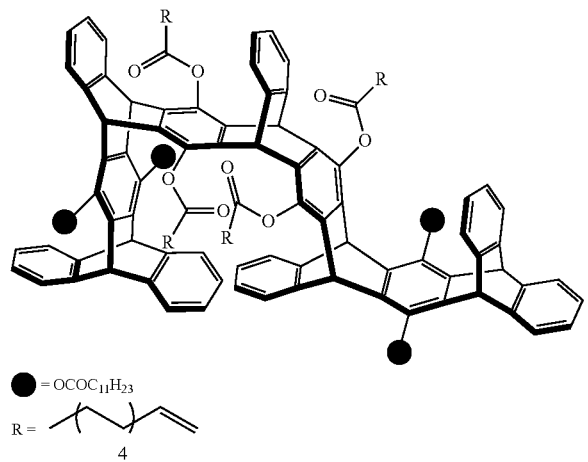

13

13: Light yellow solid. Yield: 75%. M.P.: 115-118° C. IR (ATR): 2926, 2854, 1767, 1462, 1300, 1242, 1190, 1133, 1103, 1013, 908, 750 cm$^{-1}$. $^1$H NMR (400 MHz, Chloroform-d) δ 7.18 (td, J=8.4, 3.5 Hz, 8H), 7.02 (td, J=6.3, 5.6, 3.8 Hz, 6H), 6.94-6.73 (m, 14H), 5.89 (dddd, J=16.8, 12.5, 10.2, 6.6 Hz, 4H), 5.22 (s, 2H), 5.20 (s, 2H), 5.18 (s, 2H), 5.18 (s, 2H), 5.16 (s, 2H), 5.11-4.97 (m, 8H), 2.75 (t, J=7.5 Hz, 8H), 2.73-2.62 (m, 8H), 2.14 (p, J=6.8 Hz, 8H), 2.10-1.93 (m, 16H), 1.69-1.24 (m, 104H), 0.98-0.89 (m, 12H). $^{13}$C NMR (101 MHz, Chloroform-d) δ 170.92, 170.60, 170.53, 144.39, 144.15, 143.51, 143.39, 143.32, 139.06, 138.68, 138.66, 138.61, 136.46, 135.83, 135.72, 135.58, 135.36, 135.16, 125.46, 125.37, 125.26, 124.04, 123.86, 123.77, 114.41, 114.40, 48.96, 48.88, 43.42, 43.32, 34.32, 34.29, 33.92, 33.89, 32.01, 29.81, 29.80, 29.76, 29.69, 29.66, 29.63, 29.58, 29.46, 29.32, 29.28, 29.09, 29.07, 25.64, 25.58, 25.51, 22.77, 14.19 (some of the signals are overlapped in $^{13}$C NMR). HRMS (ESI): calc m/z for $C_{168}H_{214}N_2O_{16}$ $[M+2NH_4]^{2+}$ 1258.3008, found 1258.3015.

Figure 15:
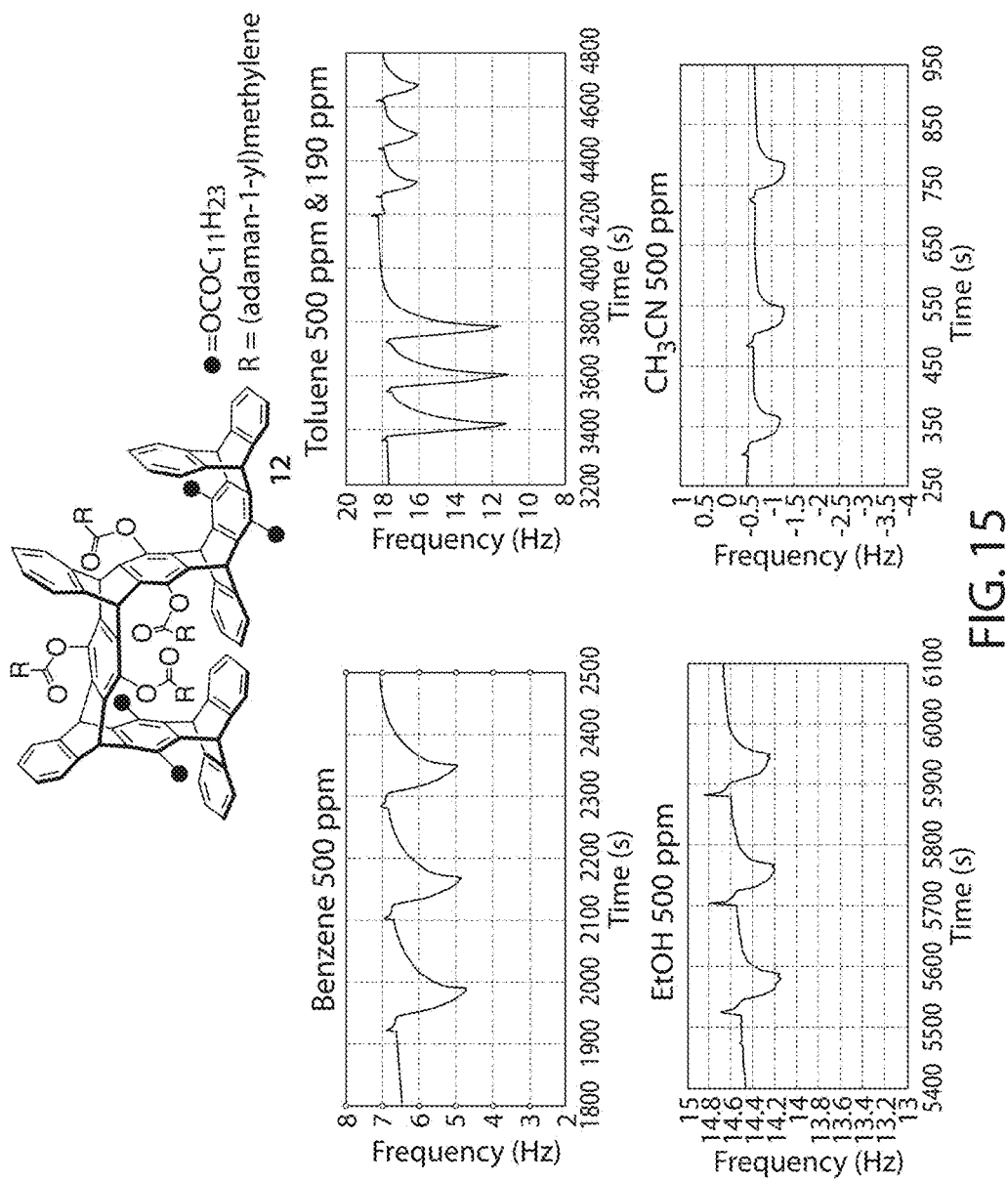
FIG. 15 shows representative QCM measurement result of the gas absorption property of absorptive materials, according to one set of embodiments.

FIG. 15 shows representative QCM measurement result of the gas absorption property of absorptive materials.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

Any terms as used herein related to shape and/or geometric relationship of or between, for example, one or more articles, structures, and/or subcomponents thereof and/or combinations thereof and/or any other tangible or intangible elements not listed above amenable to characterization by such terms, unless otherwise defined or indicated, shall be understood to not require absolute conformance to a mathematical definition of such term, but, rather, shall be understood to indicate conformance to the mathematical definition of such term to the extent possible for the subject matter so characterized as would be understood by one skilled in the art most closely related to such subject matter. Examples of such terms related to shape and/or geometric relationship include, but are not limited to terms descriptive of: shape—such as, round, square, circular/circle, rectangular/rectangle, triangular/triangle, cylindrical/cylinder, elliptical/ellipse, (n)polygonal/(n)polygon, etc.; surface and/or bulk material properties and/or spatial/temporal resolution and/or distribution—such as, smooth, reflective, transparent, clear, opaque, rigid, impermeable, uniform(ly), inert, non-wettable, insoluble, steady, invariant, constant, homogeneous, etc.; as well as many others that would be apparent to those skilled in the relevant arts. As one example, a fabricated article that would described herein as being "square" would not require such article to have faces or sides that are perfectly planar or linear and that intersect at angles of exactly 90 degrees (indeed, such an article can only exist as a mathematical abstraction), but rather, the shape of such article should be interpreted as approximating a "square," as defined mathematically, to an extent typically achievable and achieved for the recited fabrication technique as would be understood by those skilled in the art or as specifically described.

What is claimed is:

1. A method for forming a composition, comprising:
   mechanochemically reacting a first polycyclic aromatic hydrocarbon composition a comprising an anthracene, optionally substituted, with a second polycyclic aromatic hydrocarbon composition comprising a benzoquinone, optionally substituted, or an anthraquinone, optionally substituted, to form a product, wherein mechanochemically reacting comprises chemically reacting via a Diels-Alder reaction the first polycyclic aromatic hydrocarbon composition and the second polycyclic aromatic hydrocarbon composition in the presence of a mechanical force generated by mechanical milling of at least the first polycyclic aromatic hydrocarbon composition and, wherein the product comprises a bridged bicyclic-based compound comprising two or more [2.2.2] bicyclic cores, each [2.2.2] bicyclic core having the following structure:

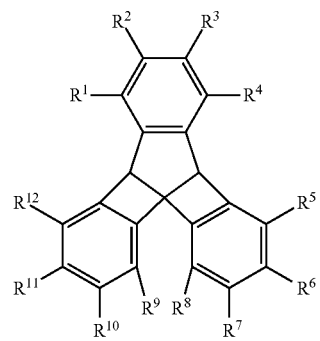

wherein:

each $R^1$-$R^{12}$ can be the same or different and are hydrogen, halo, hydroxyl, amino, alkyl, heteroalkyl, alkenyl, alkynyl, aryl, heteroaryl, heterocyclyl, or a carbonyl group, any of which is optionally substituted.

2. A composition, comprising:
   a bridged bicyclic-based compound wherein at least a portion comprises a molecular cage having a first group attached to a first [2.2.2] bicyclic core and a second group attached to a second [2.2.2] bicyclic core, wherein the bridged bicyclic-based compound has a structure as in:

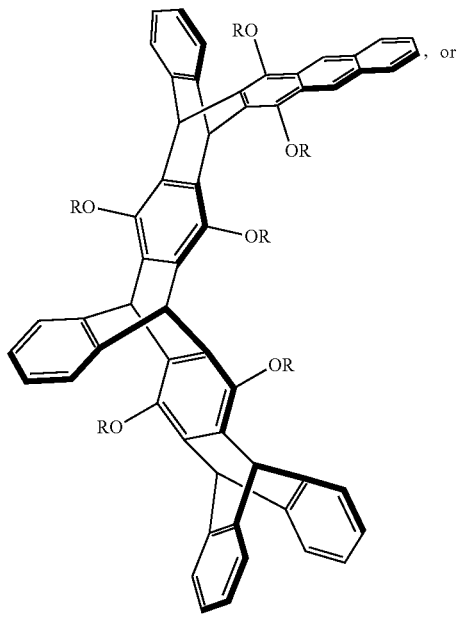

-continued

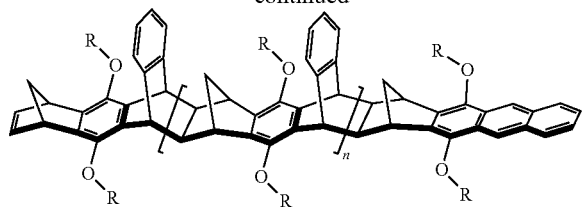

wherein:
each R can be the same or different and are hydrogen, halo, hydroxyl, amino, alkyl, heteroalkyl, alkenyl, alkynyl, aryl, heteroaryl, heterocyclyl, or a carbonyl group, any of which is optionally substituted, and n is an integer and is at least 1, further comprising:
a shortest linear distance of less than or equal to 9.5 Å between a free-end of the first group and a free-end of the second group determined without transecting the structure of the bridged bicyclic-based compound.

3. A composition as in claim 2, wherein the bridged bicyclic-based compound is formed by the mechanochemical reaction of a first polycyclic aromatic hydrocarbon composition with a second polycyclic aromatic hydrocarbon composition different than the first polycyclic aromatic hydrocarbon.

4. A composition as in claim 3, wherein the mechanochemical reaction is conducted in the presence of additives.

5. A composition as in claim 4, wherein an additive is a Lewis acid.

6. A filter device, comprising the composition as in claim 2.

7. A composition as in claim 2, wherein the bridged-bicyclic based compound has a pore size of less than or equal to 2 nm.

8. A composition as in claim 2, wherein the bridged-bicyclic based compound has a number average molecular weight of at least 1000 Da.

9. A composition as in claim 2, wherein the bridged bicyclic-based compound is an oligoiptycene.

10. A method as in claim 1, wherein the first polycyclic aromatic hydrocarbon composition with a second polycyclic aromatic hydrocarbon composition are mechanochemically reacted in the presence of additives.

11. A method as in claim 10, wherein an additive is a Lewis acid.

12. A method as in claim 1, wherein any two adjacent groups of $R^1$-$R^{12}$ are joined together to form an optionally substituted ring.

13. A method as in claim 1, wherein at least one [2.2.2] bicyclic core is an iptycene core.

* * * * *

UNITED STATES PATENT AND TRADEMARK OFFICE
CERTIFICATE OF CORRECTION

Page 1 of 1

PATENT NO. : 10,160,715 B2
APPLICATION NO. : 15/249061
DATED : December 25, 2018
INVENTOR(S) : Timothy M. Swager et al.

It is certified that error appears in the above-identified patent and that said Letters Patent is hereby corrected as shown below:

In the Claims

In Claim 1, at Column 25, Line 61, the word "a" should be removed.

Signed and Sealed this
Seventh Day of May, 2019

Andrei Iancu
*Director of the United States Patent and Trademark Office*